US010765908B1

(12) United States Patent
Uehara

(10) Patent No.: US 10,765,908 B1
(45) Date of Patent: Sep. 8, 2020

(54) SYSTEM AND METHOD FOR MUSCLE ENGAGEMENT IDENTIFICATION

(71) Applicant: Alert Core, Inc., Kailua, HI (US)

(72) Inventor: Gregory Takeo Uehara, Kailua, HI (US)

(73) Assignee: Alert Core, Inc., Kailua, HI (US)

( * ) Notice: Subject to any disclaimer, the term of this patent is extended or adjusted under 35 U.S.C. 154(b) by 121 days.

(21) Appl. No.: 16/043,695

(22) Filed: Jul. 24, 2018

Related U.S. Application Data

(63) Continuation-in-part of application No. 15/492,973, filed on Apr. 20, 2017, which is a continuation-in-part of application No. 14/789,136, filed on Jul. 1, 2015, now Pat. No. 9,706,962, which is a continuation-in-part of application No. 14/132,808, filed on Dec. 18, 2013, now Pat. No. 9,226,706.

(60) Provisional application No. 62/536,435, filed on Jul. 24, 2017, provisional application No. 62/325,196, filed on Apr. 20, 2016, provisional application No. 62/019,522, filed on Jul. 1, 2014, provisional application No. 61/739,160, filed on Dec. 19, 2012.

(51) Int. Cl.
*A63B 21/00* (2006.01)
*A63B 24/00* (2006.01)

(52) U.S. Cl.
CPC .......... *A63B 21/4001* (2015.10); *A63B 24/00* (2013.01); *A63B 2230/605* (2013.01)

(58) Field of Classification Search
CPC ............... A63B 21/4001; A63B 24/00; A63B 2230/605; A63B 21/4009; A63B 21/4011; A63B 21/4017
See application file for complete search history.

(56) References Cited

U.S. PATENT DOCUMENTS

| | | | | |
|---|---|---|---|---|
| 5,823,913 A | * | 10/1998 | Aruin | A63B 23/0244 482/4 |
| 5,980,435 A | * | 11/1999 | Joutras | A43B 1/0054 482/114 |
| 6,185,451 B1 | * | 2/2001 | Richardson | A61B 5/0488 600/546 |
| 2002/0170193 A1 | * | 11/2002 | Townsend | A61B 5/1116 33/512 |
| 2005/0043661 A1 | * | 2/2005 | Nashner | A61B 5/1038 602/26 |
| 2008/0001735 A1 | * | 1/2008 | Tran | A61B 7/00 340/539.22 |
| 2010/0234699 A1 | * | 9/2010 | Lanfermann | A63B 24/0006 600/301 |

(Continued)

*Primary Examiner* — Lisa M Caputo
*Assistant Examiner* — Philip L Cotey
(74) *Attorney, Agent, or Firm* — Staniford Tomita LLP

(57) ABSTRACT

A wearable device and system has been developed to provide feedback to help users be able to engage specific muscle groups on cue, effectively exercise said muscle groups, and learn to engage said muscle groups before and through movements. Algorithms for identifying relaxed-to-engaged and engaged-to-relaxed transitions may be important for providing a positive user experience. The wearable device and system may be used for training effective use of the core and other muscles. A myokinesiometer is described to display target muscle engagement and body movement data simultaneously. The myokinesiometer facilitates specifying tests for protected and unprotected movement analyses.

15 Claims, 24 Drawing Sheets

(56) References Cited

U.S. PATENT DOCUMENTS

| | | | | |
|---|---|---|---|---|
| 2011/0269601 | A1* | 11/2011 | Nelson | A47C 7/021 |
| | | | | 482/8 |
| 2012/0215076 | A1* | 8/2012 | Yang | A61B 5/0205 |
| | | | | 600/301 |
| 2012/0259648 | A1* | 10/2012 | Mallon | G06F 19/3418 |
| | | | | 705/2 |
| 2014/0163412 | A1* | 6/2014 | Jacobson | A61B 5/0488 |
| | | | | 600/546 |
| 2015/0250420 | A1* | 9/2015 | Longinotti-Buitoni | ...................... |
| | | | | G01L 1/22 |
| | | | | 600/301 |
| 2019/0374817 | A1* | 12/2019 | Neuberger | A61B 5/0488 |

* cited by examiner

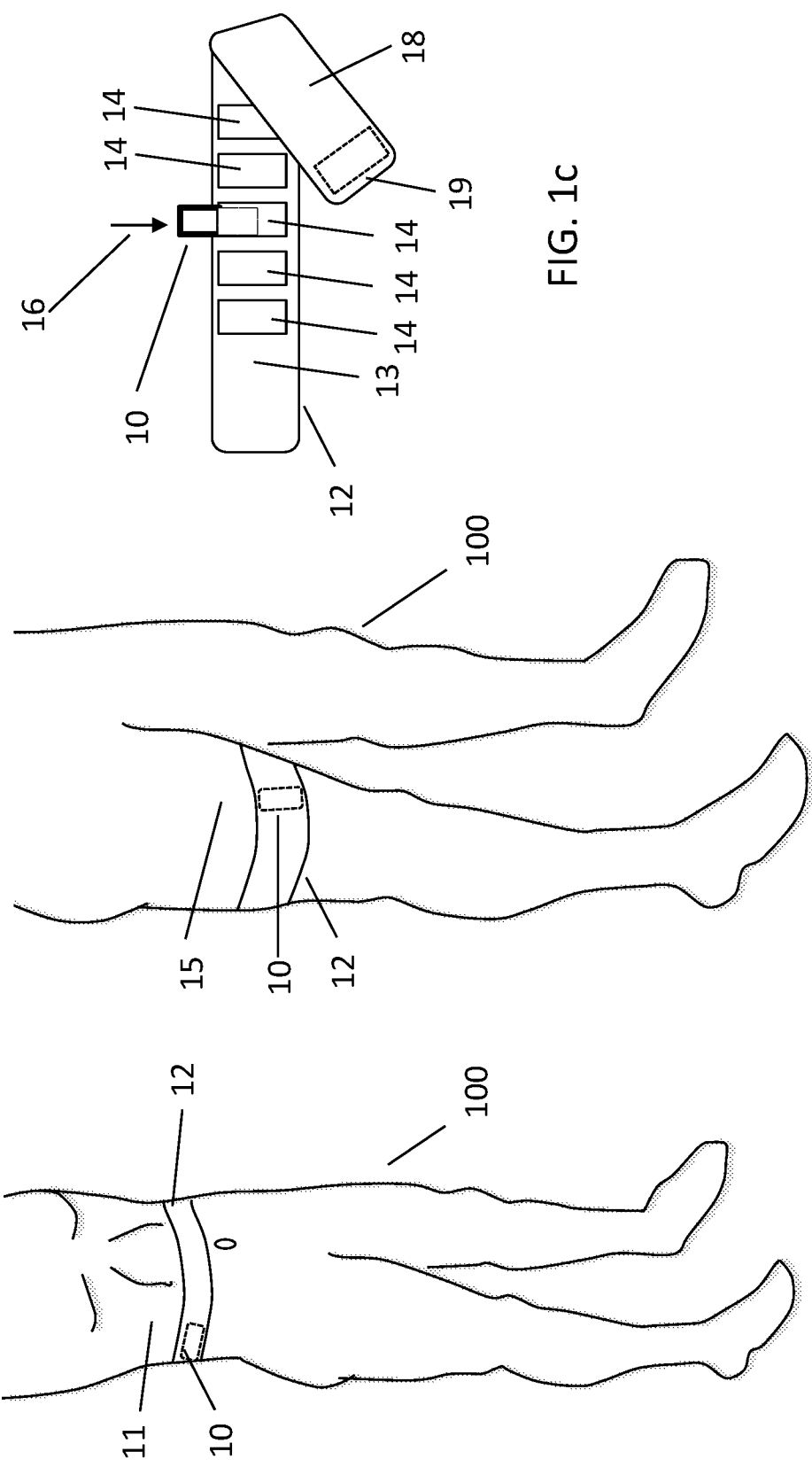

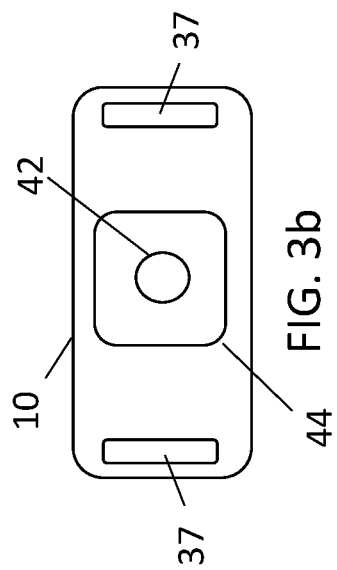
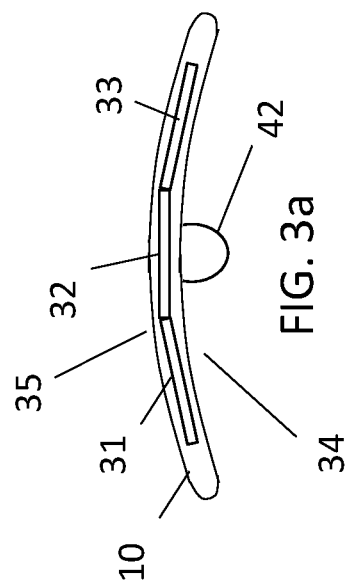

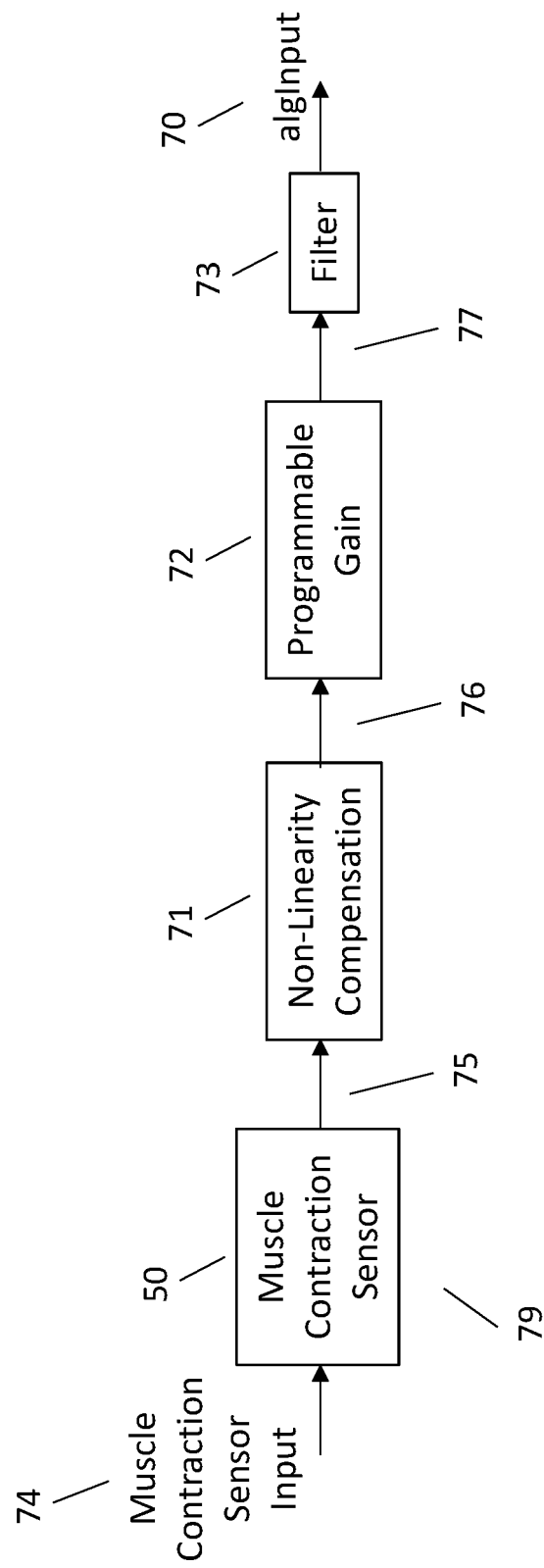

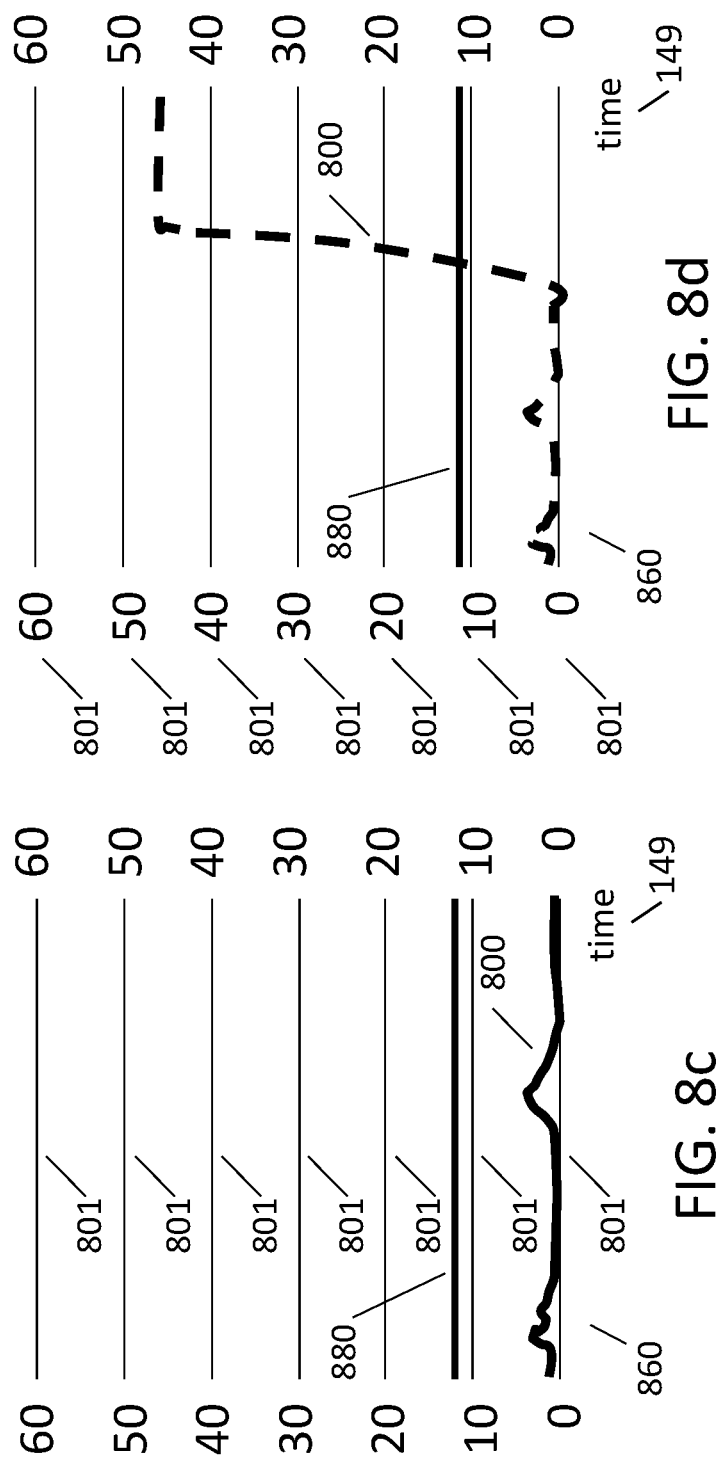

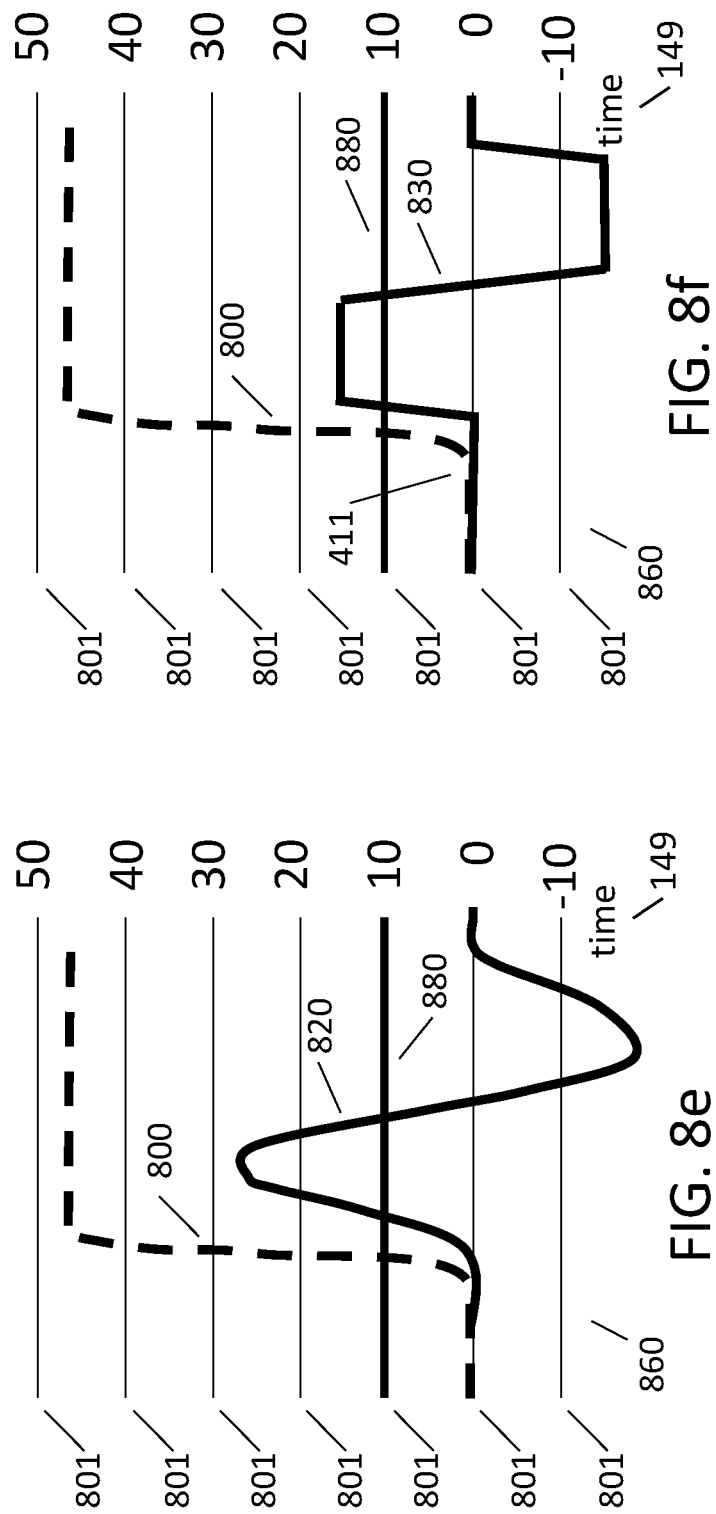

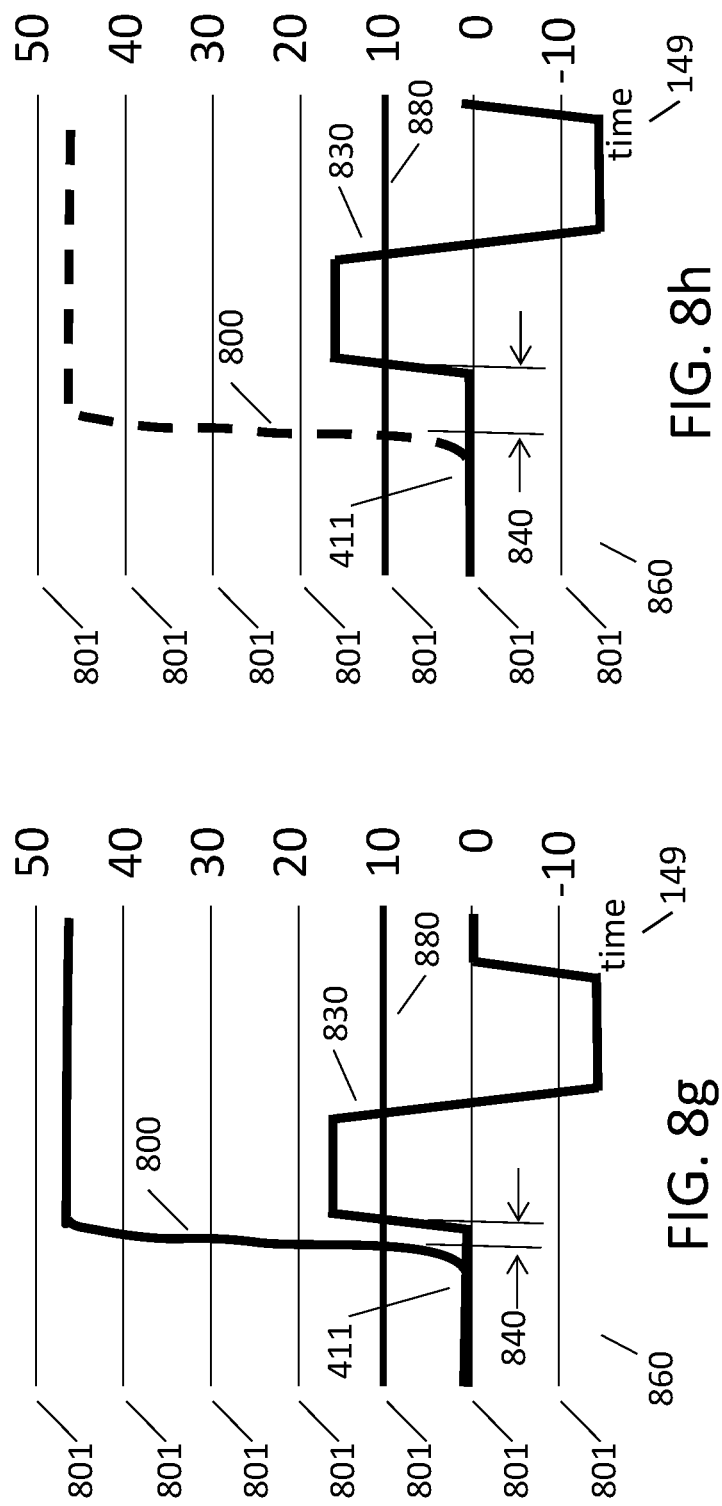

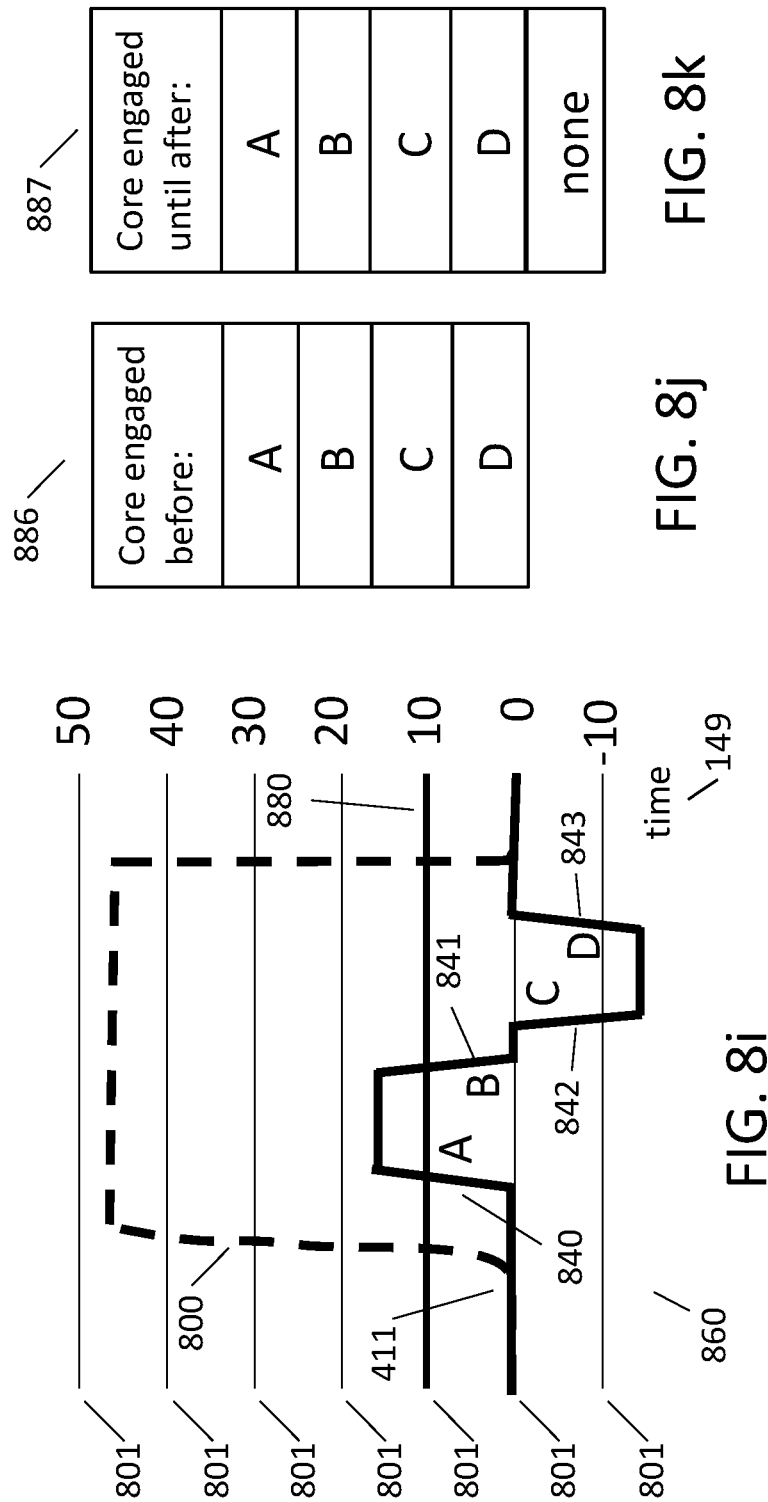

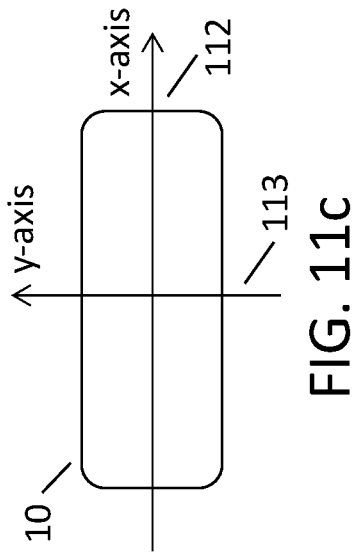
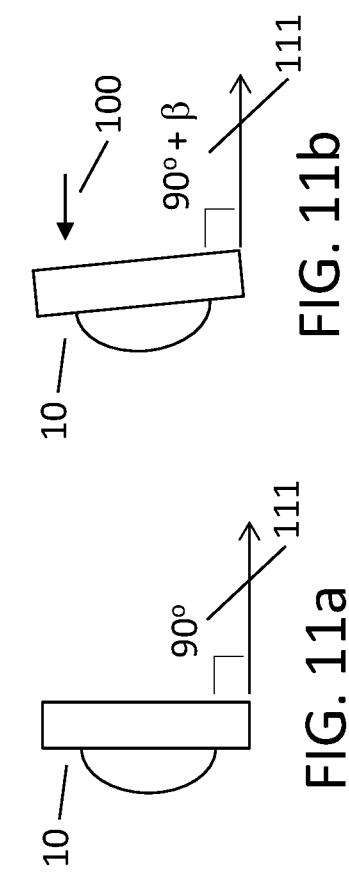
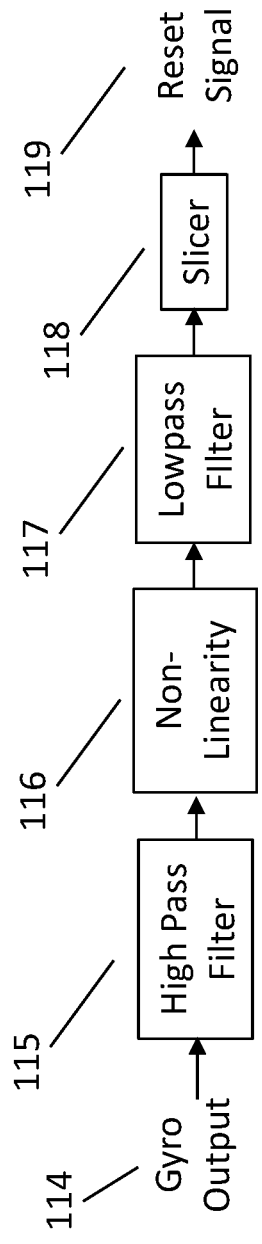

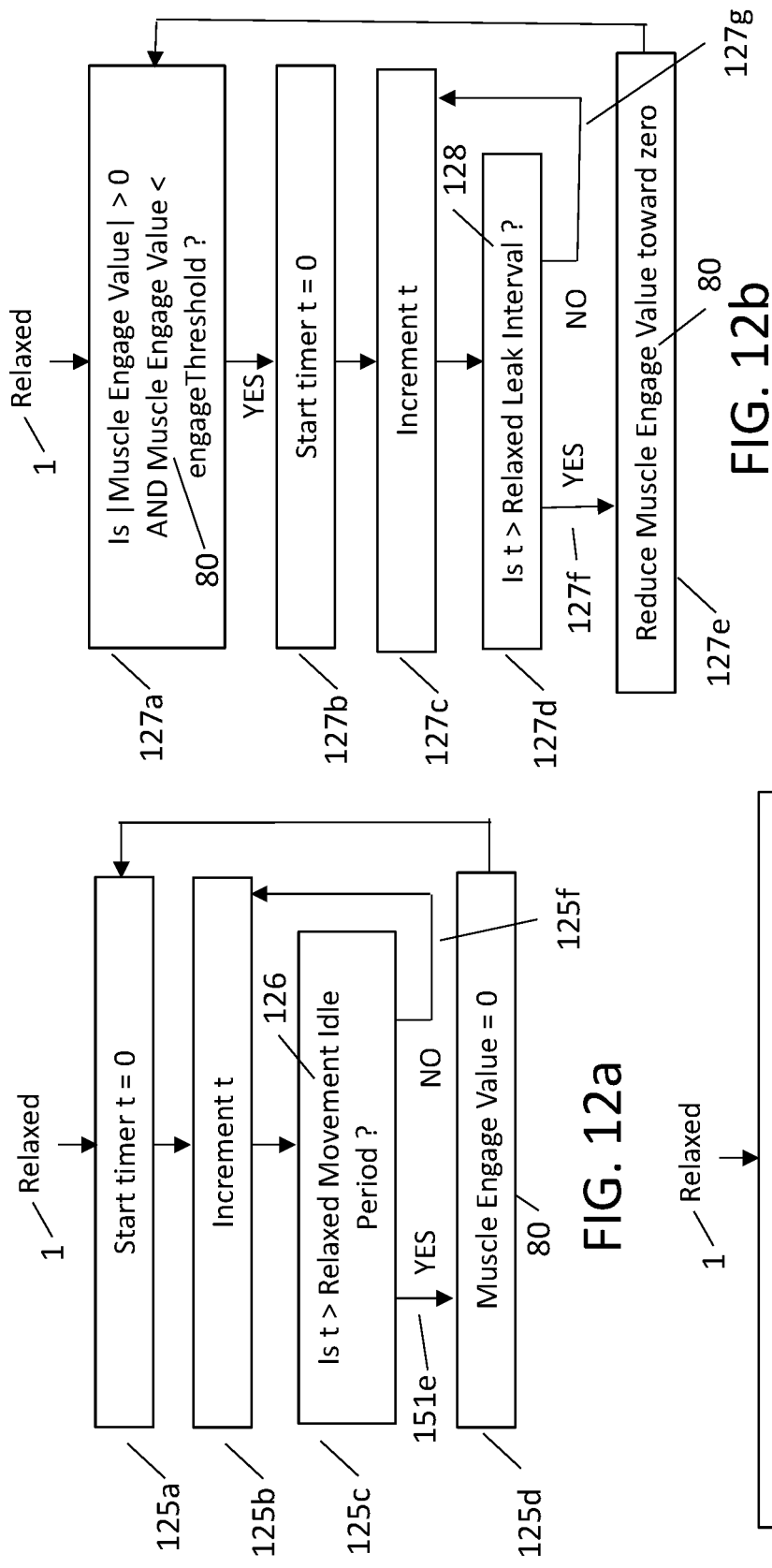

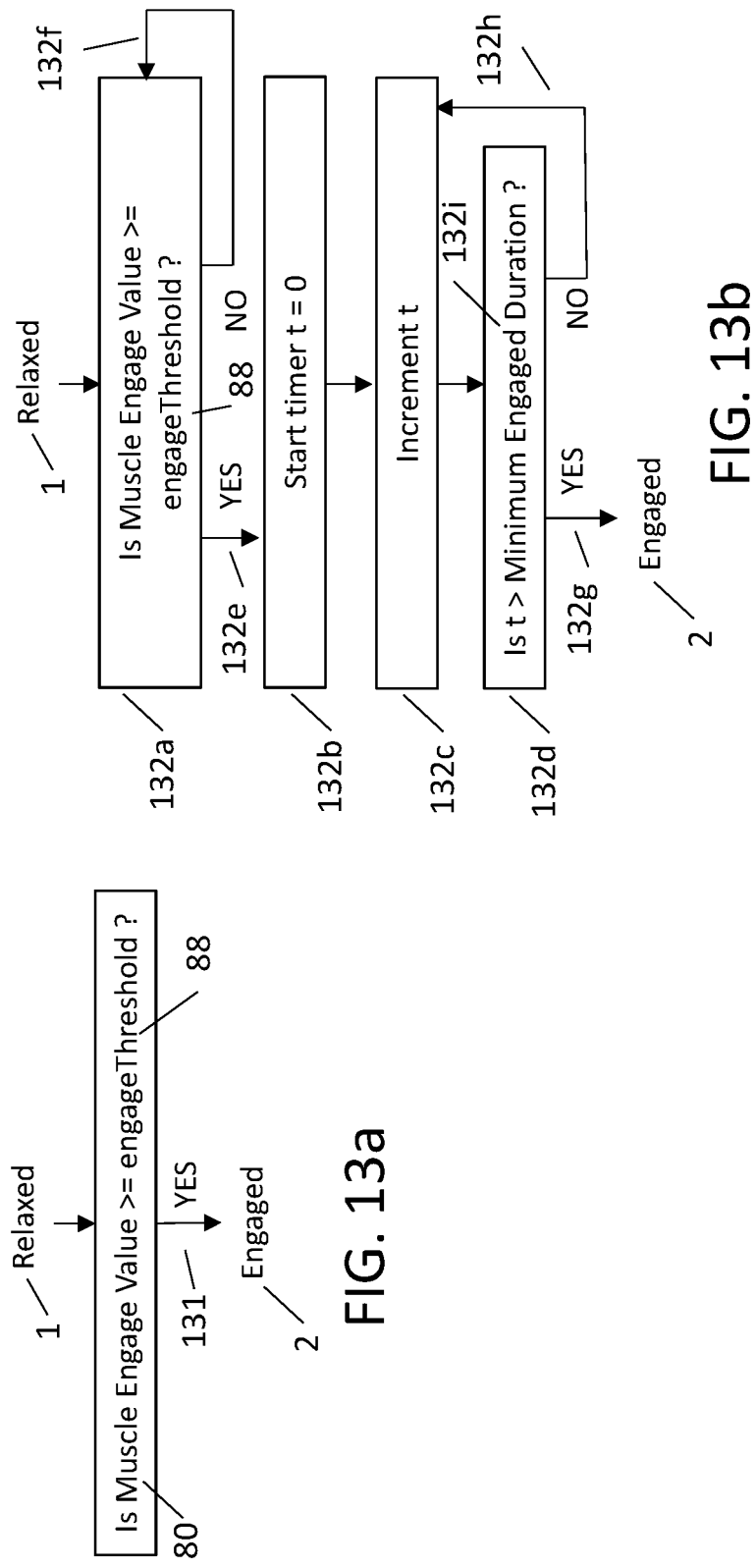

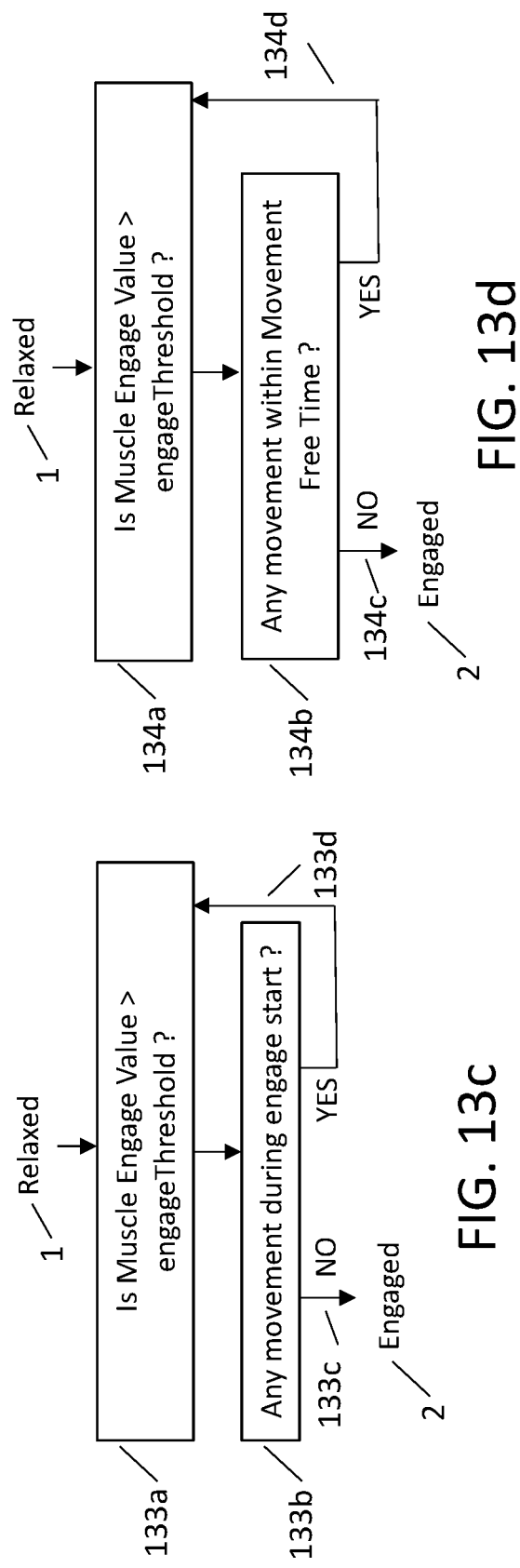

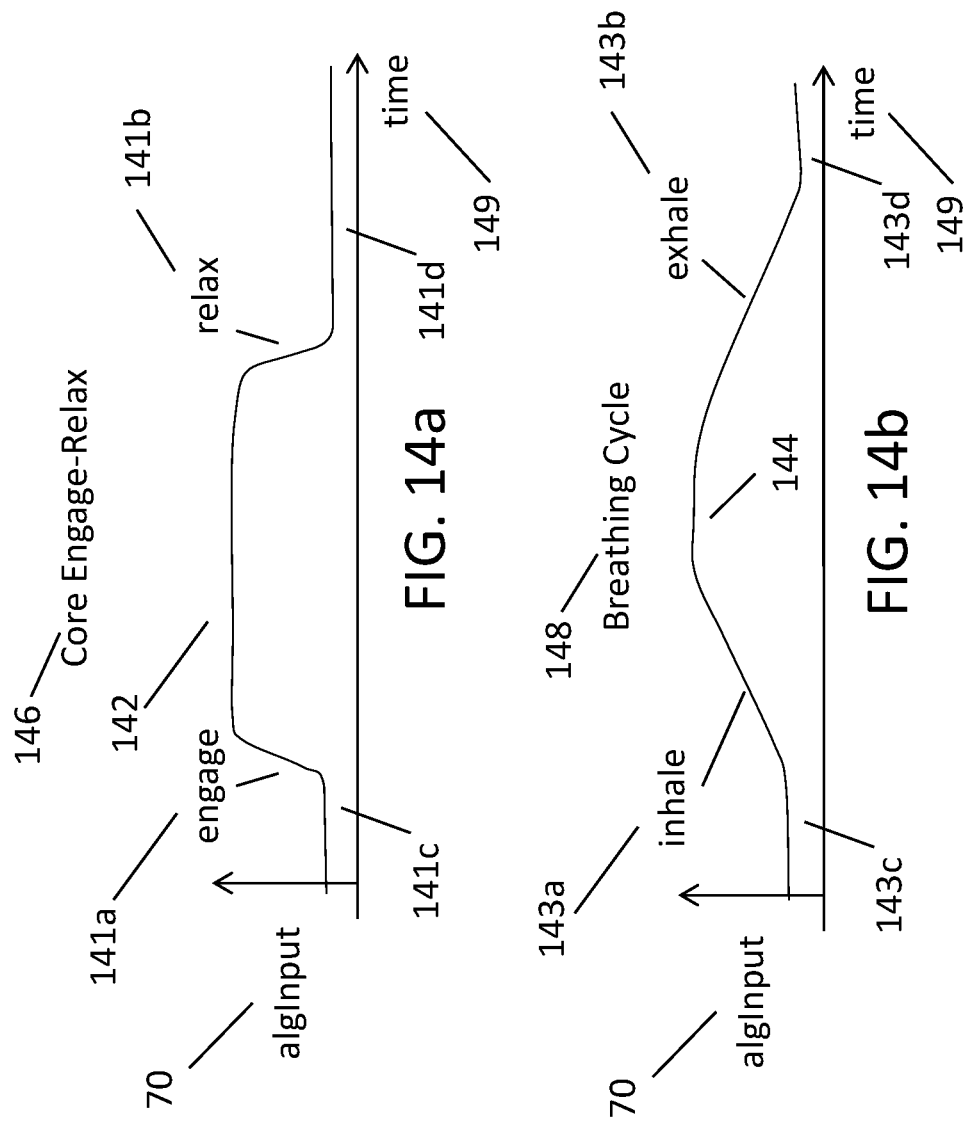

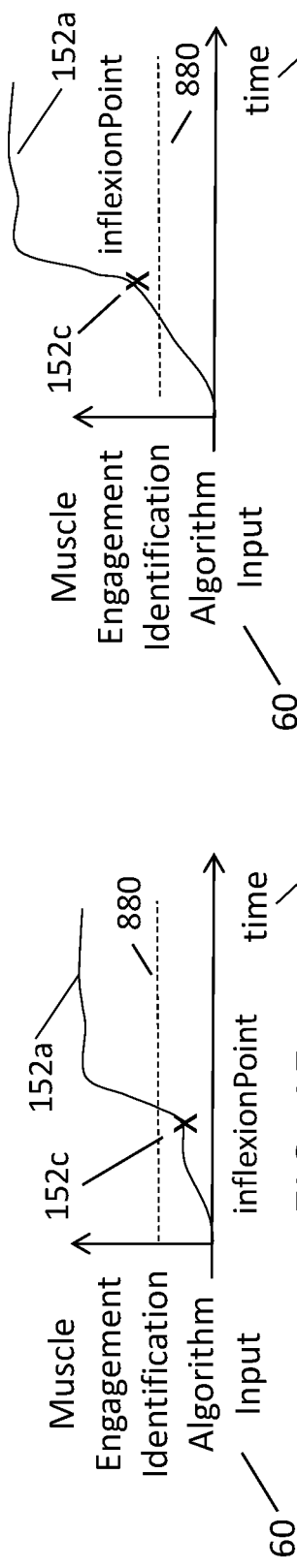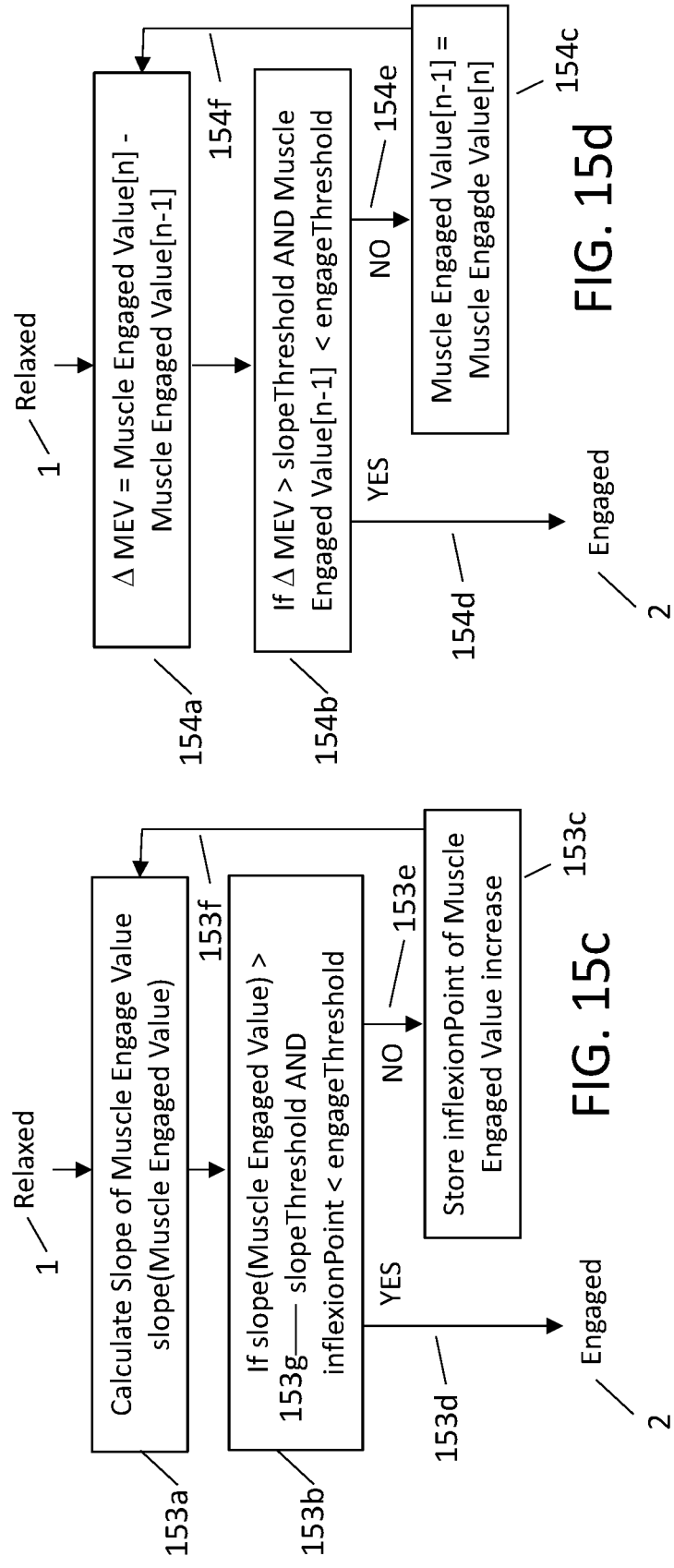

SYSTEM AND METHOD FOR MUSCLE ENGAGEMENT IDENTIFICATION

CROSS-REFERENCE TO RELATED APPLICATIONS

This application also claims priority to U.S. Provisional Application No. 62/536,435, entitled "System And Method For Muscle Engagement Identification" filed Jul. 24, 2017. This application is also a continuation in part of U.S. patent application Ser. No. 15/492,973, entitled "System And Method For Identifying Breathing Patterns During Running And Other Applications" filed Apr. 20, 2017 which claims priority to U.S. Provisional Application No. 62/325,196, entitled "System And Method For Identifying Breathing Patterns During Running And Other Applications", filed Apr. 20, 2016. U.S. patent application Ser. No. 15/492,973 is also a continuation in part of U.S. patent application Ser. No. 14/789,136, entitled "Apparatus And Method For Teaching And Algorithms For Identifying Qualifying Movements", filed Jul. 1, 2015, now U.S. Pat. No. 9,706,962, which claims priority from U.S. Provisional Application No. 62/019,522, entitled "Apparatus And Method For Teaching And Algorithms For Identifying Qualifying Movements", filed Jul. 1, 2014. U.S. patent application Ser. No. 14/789,136 is a continuation in part of U.S. patent application Ser. No. 14/132,808, entitled "System, Apparatus, And Method For Promoting Usage Of Core Muscles And Other Applications", filed Dec. 18, 2013, now U.S. Pat. No. 9,226,706 which claims priority to U.S. Provisional Application No. 61/739,160, entitled "System For Promoting Usage Of Core Muscles And Other Applications", filed Dec. 19, 2012. The disclosures of U.S. patent application Ser. Nos. 15/492,973, 14/132,808, 14/789,136, 62/536,435, 62/325,196, 62/019,522, and 61/739,160 are hereby incorporated herein by reference in their entirety. The aforementioned patent references are referred to as "Incorporated Patent References."

FIELD OF THE INVENTION

Embodiments disclosed relate to systems and methods for development of core muscle support for back pain rehab, injury prevention, and performance improvement. Embodiments also relate to systems and methods for isolating and exercising other muscles for physical therapy rehab and strength conditioning. These other muscles may include the gluteus maximus, gluteus medius, hamstrings, quadriceps, biceps, triceps, muscles of the forearm, calf muscles, latissimus dorsi, pecs, and others. Embodiments relate to algorithms for identifying relaxed-to-engaged and engaged-to-relaxed transitions in different applications. Embodiments relate to tools for viewing and analyzing the coordination of muscle engagement with body movements.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be embodiments of the invention.

In recent years, there has been explosive growth in the number of portable and handheld devices that include but are not limited to sensors such as accelerometers, gyros, magnetometers, altimeters, force, and/or pressure sensors. Examples of such devices include smart phones, cell phones, gaming devices, and wearable devices or "wearables." A large number of wearables target health and fitness applications where steps taken and flights of stairs taken by device users are tracked utilizing accelerometers and altimeters. Most health and fitness wearables on the market today may track one or more of the following: steps taken, number of stairs taken, heart rate, movement activity, and sleep patterns. These devices generally utilize accelerometers, altimeters, light sources and sensors, and voltage sensors to sense and detect the parameters they measure and track.

In physical therapy rehab, training to improve physical and athletic performance, and training for injury reduction, there is often a need to engage or contract a specific muscle or muscle group to target their use during exercise, or to engage a specific muscle or muscle group before and throughout a movement to provide support. However, without a feedback device on the targeted muscle or muscle group, it may be difficult for the subject to isolate and engage the muscle or muscle group. While the subject may engage the targeted muscle or muscle group before the movement, the subject may relax during the movement. Without a feedback device providing continuous feedback, it may be difficult to identify if the subject engaged the muscle or muscle group before and throughout the movement. An example of a muscle group and a movement in which engaging the target muscle group before and throughout the movement may include engaging the core muscles before and throughout standing up from a seated position during a episode of back pain.

In therapy rehab, isolating muscles is important for muscle re-education that is often required after injury or surgery. Isometric exercises are physical exercises in which muscles are caused to act against each other or against a fixed object. Isometric exercises may involve engaging or contracting a muscle or muscle group and keeping it engaged for a period of time. For some applications, the period of time may be 30 seconds. For some applications, the period of time may be longer than 30 seconds, For other applications it may be shorter than 30 seconds. It may be beneficial when doing isometric exercises to have a means to confirm that the target muscle or muscle group is indeed engaged during the exercise and a minimum degree of engagement intensity is being maintained. In isotonic exercises, the muscles maintain the same tension throughout the exercise. If a target muscle in an isotonic exercise can be engaged before and through the exercise, the exercise may be more beneficial for the target muscle and further aid the subject's neuromuscular system with muscle education or re-education. An appropriate feedback device for isometric and isotonic exercises that can provide an indication of engagement intensity can be beneficial for improving the quality and thus, the benefits of said exercises. Quantitative feedback can also provide motivation for the subject to make measurable improvements or compete with a partner.

For performance training and injury reduction training, both isometric and isotonic exercises may play important roles. The ability to engage specific target muscles may increase the effectiveness of such exercises. Further, with an appropriate training regimen, a connection between the brain and the target muscle may be established and developed to build motor memory for conscious deliberate use of that muscle and eventually an automatic use of that muscle in specific tasks.

In the exercise settings of a therapy clinic, in-home therapy with a therapist and patient, and in gym training, there may be need to quickly transition exercises emphasizing one muscle or muscle group to another. For example, in one exercise set the core muscles may be the target muscle group. In the next exercise set, the gluteus maximus may be the target muscle. The ability to move the monitoring device quickly and conveniently may be important in some applications.

One approach to monitoring muscle engagements uses electromyography (EMG). Electromyography measures electrical activity in a muscle. One form of EMG, needle EMG, utilizes insulated needles each with a small region of bare metal that is inserted into a muscle to make direct electrical contact that the muscle. Due to its invasive nature, needle EMG is not widely used in therapy and gym settings. Another form of EMG is called surface EMG where electrodes are attached to the surface of the skin over the region of the target muscle. The good electrical contact needed between the electrodes and the skin may be achieved in different ways. Conductive gels may be used on the electrodes as they are held against the skin using tape.

Some of the newer electrodes have built-in adhesives that stick to the skin. These sticky surface electrodes need to be replaced after a number of uses. Surface EMG is not as accurate as needle EMG but sufficient for most clinical and gym applications. Sticky surface electrodes, while being much simpler than the needle electrode counterpart may be a bit cumbersome to move from one muscle or muscle group to another.

Another approach to monitoring muscle engagements uses ultrasound. While potentially being very accurate, ultrasound probes are expensive and require gels to make effective contact to the skin. Implementations to date make body movement while monitoring a muscle difficult.

The wearable device and app that runs on a smart device or dedicated device that has been described in Incorporated Patent References may be used to monitor the relaxed and engaged status of a muscle or muscle group, and provide immediate feedback; can be quickly moved from one muscle or muscle group to another when held against the body with an appropriate attachment device, for example, a belt or strap; does not require any gels or special probes requiring direct contact to the skin; and can be used over most clothing. In applications where more than one muscle or muscle group must be monitored during the same exercise, multiple wearable devices may be used.

Protected movements involve movements which benefit the user when a target muscle is engaged before and through the movement or critical aspects of the movement. Unprotected movements involve movements in which a target muscle is not contracted adequately to have made the movement a protected movement. Protected movements may benefit a user by improving an exercise, improving a rehab movement, result in a movement with less likelihood of injury, improve an athletic movement, contribute to procedural memory development for use of the target muscle in the movement, or have another desirable short term or long term result. Protected qualifying movements are protected movements.

In this patent application, techniques and algorithms to improve the performance and utility of the wearable device and system are described.

SUMMARY OF THE INVENTION

A wearable device and system are designed to provide immediate feedback to assist a user in connecting with, exercising, and developing motor habits of utilizing muscles before and through movements.

In an embodiment, a wearable device contributes to providing feedback for a contraction of a muscle or muscle group using pressure sensing or force sensing with a bumper which couples the sensor to the target muscle or muscle group.

In an embodiment, a wearable device contributes to providing feedback for a contraction of a first muscle or muscle group is held against the body over said muscle or muscle group for a first exercise, then moved over a second muscle or muscle group for monitoring the second muscle or muscle group for a second exercise. In an embodiment, the wearable device is held over the first muscle or muscle group with a belt or strap and held over the second muscle or muscle group with the same belt or strap. In an embodiment, the wearable device is held over the first muscle or muscle group with a first belt or strap and held over the second muscle or muscle group with a second belt or strap. In an embodiment, the wearable device may be used over the user's clothing, including muscles of the core, muscles of the torso, muscles of the arms, or muscles of the legs.

In an embodiment, the belt or strap may use a quick attachment element to enable the wearable device to be moved from a first muscle or muscle group to a second muscle or muscle group quickly. In an embodiment, the portion of the belt or strap encircling the body part containing the muscle or muscle group to be monitored may be partially or substantially elastic. In an embodiment, the belt or strap may have a pocket for quickly sliding in the wearable device to attach the wearable device to the belt or strap. In an embodiment, the belt or strap may have a multiplicity of pockets to facilitate using the belt or strap for placing the device over different muscles or muscle groups. In an embodiment, the multiplicity of pockets may have include at least one pocket in a different orientation from the other pockets. In an embodiment, the belt or strap may use hook and loop elements for quick attachment and detachment. In an embodiment, the belt or strap may use snaps, magnets, buckles, or other elements for quick attachment and detachment.

In an embodiment, the wearable device includes a muscle contraction sensor. In an embodiment, the muscle contraction sensor utilizes a pressure or force sensor. In an embodiment, the pressure or force sensor couples to the target muscle or muscle group via a bumper. In an embodiment, the bumper may couple to a first interchangeable element that may result in a first bumper or first composite bumper with a first height and girth; and the bumper may couple to a second interchangeable element that may result in a second bumper or second composite bumper with a second height and girth. In an embodiment, the interchangeable element may be an extender cap.

In an embodiment, the muscle contraction sensor may be placed into a muscle contraction sensor circuit. In an embodiment, the muscle contraction sensor circuit is configured for the output signal to increase as pressure or force on the muscle contraction sensor increases. In an embodiment, the output signal of the muscle contraction sensor circuit is processed by a Muscle Engagement Identification Algorithm running on a processor. In an embodiment, the output signal of a muscle contraction sensor is output directly to the processor. In an embodiment, the output signal of a muscle contraction sensor may decrease as pressure on the muscle contraction sensor increases. A signal processing compensation block may follow the contraction sensor to change the polarity of the output signal to result in the output signal of the compensation block increasing as the pressure on the muscle contraction sensor increases.

In an embodiment, the Muscle Engagement Identification Algorithm (Algorithm) may contain at least two states. In an embodiment, the states may be represented in a state diagram. In an embodiment, a first state may be associated with the target muscle being identified as relaxed and a second state may be associated with the target muscle being identified as engaged. In an embodiment, a third state may be associated with the target muscle being identified as engaged when the identified muscle is relaxed. In an embodiment, the system may report a Muscle Engaged Value corresponding to a status of a target muscle or muscle group to the user. In an embodiment, the Muscle Engaged Value may be called the Core Value or Core Score when the target muscle or muscle group is the core. In an embodiment, the Muscle Engaged Value may be given another name or be referred to by another name.

In an embodiment, when the muscle is relaxed, the Muscle Engaged Value may have a nominal value. In an embodiment, when the muscle is relaxed, the Muscle Engaged Value may have a nominal value of zero. In an embodiment, as the muscle begins to firm and engage, the Muscle Engaged Value may increase. In an embodiment, when the body moves causing pressure on the muscle contraction sensor to decrease or if the monitored region of the body retracts, the Muscle Engaged Value may be held at a Relaxed Minimum Value. In an embodiment, the Relaxed Minimum Value may be zero.

In an embodiment, when the Muscle Engaged Value is constrained by a Relaxed Minimum Value and greater than the Relaxed Minimum Value and less than the engageThreshold, this value of the Muscle Engaged Value may persist indefinitely. In an embodiment, when the Muscle Engaged Value is greater than the Relaxed Minimum Value and less than the engageThreshold, the Muscle Engaged Value may be decremented to leak toward zero over a period of time. In an embodiment, when the Muscle Engaged Value is less than zero and not constrained by a Relaxed Minimum Value, while the relaxed state persists, the Muscle Engaged Value may be decremented to leak to zero over a period of time.

In an embodiment, the transition from the relaxed state to the engaged state may occur when the Muscle Engaged Value is equal to or greater than an engageThreshold. In an embodiment, the engageThreshold may be a fixed value. In an embodiment, the system parameters may be set up so that the Muscle Engaged Value corresponding to a maximum voluntary contraction (MVC) is in the range between eighty (80) and one hundred (100). In an embodiment, the engageThreshold may be ten (10) in a system parameterized so that the Muscle Engaged Value corresponding to an MVC is in the range between eighty (80) and one hundred (100). In an embodiment, the engageThreshold may be programmable by the user.

In an embodiment, when the Muscle Engaged Value exceeds the engageThreshold, the system may provide immediate feedback indicating the transition from the relaxed state to the engaged state. In an embodiment, the Muscle Engaged Value must additionally maintain a value equal to or greater than the engageThreshold for a minimum engaged period of time. In an embodiment, the minimum engaged period of time may be one second. In an embodiment, the minimum engaged period of time may have a value less than one second. In an embodiment, the minimum engaged period of time may have a value greater than one second.

In an embodiment, in addition to exceeding the engageThreshold to trigger a transition from relaxed to engaged, there may be an additional constraint that the Muscle Engaged Value increase with a minimum slope. In an embodiment, the point at which an increase in the slope of the Muscle Engaged Value above a minimum slope may identify an inflexionPoint. In an embodiment, if the inflexion point occurs below a first threshold and the subsequent slope of the Muscle Engaged Value exceeds a second threshold, a transition from relaxed to engaged may be triggered. Whereas if the inflexion point occurs above the first threshold, then a transition from relaxed to engaged may not be triggered even if the subsequent slope of the Muscle Engaged Value exceeds the second threshold. This may be used in an application to differentiate an inhale or breath in from a core engagement.

In an embodiment, in addition to the Muscle Engaged Value exceeding the engageThreshold, a relaxed to engaged transition may be triggered only if the movement sensors detect little or no body movement at the moment the engageThreshold is exceeded. In an embodiment, in addition to the Muscle Engaged Value exceeding the engageThreshold, a relaxed to engaged transition may be triggered only if the movement sensors detect little or no body movement for a period of time (Movement Free Time) following the Muscle Engaged Value exceeding the engageThreshold. In an embodiment, the Movement Free Time may be approximately 250 msec. In an embodiment, Movement Free Time may be less than or more than 250 msec.

In an embodiment, once in the engaged state, when the Muscle Engaged Value becomes less than the engageThreshold, the state may return to the relaxed state. In an embodiment, when the state transitions from the engaged state to the relaxed state, the system may provide immediate feedback.

In an embodiment, when the state transitions from the relaxed state to the engaged state, the Algorithm may begin tracking the Muscle Engaged Value with a Muscle Engaged Value Tracker. The Muscle Engaged Value Tracker output, the Tracked Engaged Value, may contain an estimate of the Muscle Engaged Value for a particular muscle engagement. In an embodiment, the Muscle Engaged Value Tracker may utilize filtering. In an embodiment, the Muscle Engaged Value Tracker may also utilize gear shifting. In an embodiment, when the Muscle Engaged Value reduces below the Tracked Engaged Value output minus a relaxThreshold, the state may return to the relaxed state. In an embodiment, the relaxThreshold may equal the engageThreshold. In an embodiment, the relaxThreshold may be a fraction of the Tracked Engaged Value. In an embodiment, the relaxThreshold may be a variable fraction of the Tracked Engaged Value determined by look-up table. In an embodiment, use of the Tracked Engaged Value minus the relaxThreshold in an engaged to relaxed trigger, reset of the Muscle Engaged Value to zero (0) upon said engaged to relaxed trigger, and a Relaxed Minimum Value of zero (0) may be used together to crisply transition the Muscle Engaged Value to zero (0) and prepare the system for the next engagement of a target muscle.

In an embodiment, the algorithm used to transition from the engaged state to the relaxed state may depend on the Tracked Engaged Value. If the Tracked Engaged Value is less than a threshold value, for example twice the engageThreshold, the algorithm may identify the transition from engaged to relaxed when the Muscle Engaged Value becomes less than the engageThreshold. In an embodiment, a relaxThreshold may be used in place of the engageThreshold to identify the transition from engaged to relaxed wherein the relaxThreshold is less than the engageThreshold in order to introduce hysteresis. If the Tracked Engaged Value is greater than a threshold value, for example twice the engageThreshold, then the Algorithm may utilize the Tracked Engaged Value. For an application, other conditions may be used to select a threshold to trigger an engaged to relaxed transition.

In an embodiment, if movement is detected by the movement sensors, when an engaged to relaxed trigger is identified, the trigger may be inhibited until the movement has stopped or reduced below a certain level.

In an embodiment, if the system is in the engaged state for a period longer than the Maximum Engage Duration, the Algorithm may trigger an engaged to relaxed transition. In an embodiment, the Maximum Engage Duration may be 4 seconds. In an embodiment, the Maximum Engage Duration may be user programmable.

In an embodiment, if the system is in the engaged state and the user's muscle is relaxed, the user may force the algorithm to return to the relaxed state by touching an element on the app. In an embodiment, the app feature for forcing a return to the relaxed state may be a button. In an embodiment, the app feature for forcing a return to the relaxed state may be a graph. In an embodiment, the app feature for forcing a return to the relaxed state may be a Muscle Engage Circle. In an embodiment, the app feature for forcing a return to the relaxed state may be a myokinesiograph.

In an embodiment, if the system is in the engaged state and the user's muscle is relaxed, the user may force the algorithm to return to the relaxed state by physically manipulating the wearable device in a unique way. In an embodiment, the unique way to manipulate the wearable device may result in movement of the device that may be unlikely to occur in normal operation. In an embodiment, the movement may include a fast toggle about the x-axis. In an embodiment, the movement may include another movement about an axis or plane of the wearable device.

In an embodiment, a 100% Maximum Voluntary Engagement or 100% MVE may be identified wherein the user may engage a target muscle to its maximum contraction intensity and a maximum Muscle Engaged Value (MVE) may be provided by the wearable device and app. When the user relaxes the target muscle, 0% MVE may be identified at a Muscle Engaged Value of 0. In an embodiment, MVE may be used in the app for different applications. In an embodiment, MVE is acquired and MVE is used in an exercise intensity target with little or no change in position of the wearable device over the target muscle and little or no change in belt tightness between MVE acquisition and use in the exercise target. In an embodiment, MVE may be used as the target or a % of MVE may be used as the target intensity for the exercise. In an embodiment, MVE acquisition and MVE use in an exercise target may be used in an isometric exercise. In an embodiment, MVE acquisition and MVE use in an exercise target may be used in an isotonic exercise.

In an embodiment using MVE acquisition and MVE use in an exercise target for an isometric exercise, at the beginning of the exercise, the user may be advised to engage the target muscle to its maximum contraction intensity for a short period of time. In an embodiment, the short period of time may be four (4) seconds. The MVE may be recorded by the app. After a brief rest, the user may be advised to perform an isometric hold of the target muscle for the duration of one rep of the exercise at an intensity normalized to a percentage of MVE. In an embodiment, the user may specify a target percentage of MVE for each rep the app is programmed to have the user perform. In an embodiment, the percentage of time the user exceeds the target percentage of MVE during a rep may be used to calculate a score for that rep. In an embodiment, other scoring methods may be utilized. In an embodiment, the score may be stored and reported to the user. In an embodiment, the score may be reported to others such as a therapist, trainer, coach, or doctor. To illustrate, a user may program three (3) reps of thirty (30) seconds each. The user may program 95% MVE for rep 1, 90% MVE for rep 2, and 85% MVE for rep 3.

A myokinesiometer may be implemented by the wearable device and app. A myokinesiometer is a tool for acquiring data (via the wearable device) and displaying muscle (myo) data and movement (kinesio) data simultaneously for muscle training and muscle retraining, effective exercising, and motor skill or procedural memory development. In an embodiment, the myokinesiometer may provide display and audio feedback, and buzzing within the wearable device to identify protected or unprotected qualifying movements or protected or unprotected movements. In an embodiment, the myokinesiometer may display and measure time between events such as a target muscle engaging and the start of a body rotation. In an embodiment, the myokinesiometer may display and provide feedback if an event such as engaging a target muscle does not occur a minimum time duration before the start of a body rotation. In an embodiment, the myokinesiometer may display and allow the user to test the engagement of a target muscle and to evaluate if the target muscle is engaged before a first movement event and if the target muscle stays engaged through a second movement event. Depending on the timing relationships of the events, feedback may be provided as to whether a movement is protected or unprotected. Feedback may also be provided simply, if a first event occurs as desired before a second event. Feedback may be provided if a first event occurs as desired a minimum time period before a second event. Feedback may be provided if a first event does not occur as desired a minimum time period before a second event. In an embodiment, the myokinesiometer may contain a graphical user interface that facilitates selection of a first movement event and a second movement event from a number of events. Sensor gyro data output is proportional to instantaneous angular velocity. Gyro data may be converted to rotation data by slicing the gyro data using a thresholding function. Each rotation may be simplified as having a start of rotation and an end of rotation. In an embodiment, the myokinesiometer may have a graphical user interface to enable the user to quickly select which edges of which rotations to use in qualifying movement and protected movement analyses. In a basic movement like sit-to-stand, there may be two rotations and four rotation events. The graphical user interface may facilitate selecting a first movement event and a second movement event from the four rotation events. Based on the timing of events, feedback may be provided to the user. In addition to getting events in a certain order, the myokinesiometer may also facilitate verification that an event occurs a minimum time period before another event. For example, if the core is not engaged at least 250 msec before a body rotation, feedback may be provided.

In an embodiment, the myokinesiometer may allow the user to make sensor selections, measure different characteristics and timing relationships between a target muscle engagement and specific aspects of body rotations, body movements, body orientations, or body elevations. In an embodiment, rotation, orientation, and elevation may be analyzed depending on available sensors in the wearable device.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 1a illustrates a position of the wearable device worn over the core muscles of a user.

FIG. 1b illustrates a position of the wearable device worn over the quadriceps of a user.

FIG. 1c illustrates an embodiment of a belt with multiple pockets to facilitate use around different body parts and different user body sizes.

FIG. 3a illustrates a side view of the wearable device.

FIG. 3b illustrates a front view of the wearable device from the perspective of the face of the device which couples to the target muscle.

FIG. 7 illustrates a block diagram from the muscle contraction sensor, non-linearity compensation, gain control, and filtering to generate the muscle engagement identification algorithm input.

FIG. 8c-FIG. 8h illustrates myokinesiograph displaying plots of target muscle engagement and sensor or movement data over time. Timing relationships between target muscle engagement and movement data may be observed.

FIG. 8i-FIG. 8k illustrates use of a graphical user interface to identify aspects of movement data to use in protected and unprotected movement analyses.

FIG. 11a-FIG. 11c illustrates one approach to manipulate the wearable device to physically bring about a reset.

FIG. 11d illustrates a block diagram of a signal processing path the generate a reset signal from the physical toggling associated with movements of the device shown in FIG. 11a-FIG. 11c.

FIG. 12a-FIG. 12c illustrates signal flow diagrams for embodiments to keep the device in the relaxed state and ready to respond to changes in the target muscle.

FIG. 13a-FIG. 13d illustrates signal flow diagrams for embodiments for transitioning from the relaxed state to the engaged state.

FIG. 14a-FIG. 14b illustrate a possible difference in the muscle engagement identification algorithm input when the target muscle is the core muscles and the user engages their core compared to when the user inhales a breath of air.

FIG. 15a-FIG. 15b illustrates the definition of the inflexionPoint and its use in differentiating between a core engagement and inhaling a breath of air.

FIG. 15c-FIG. 15d illustrates signal flow diagrams for embodiments to minimize false identification of inhaling a breath of air as a core engagement.

DETAILED DESCRIPTION

Figure 2B:
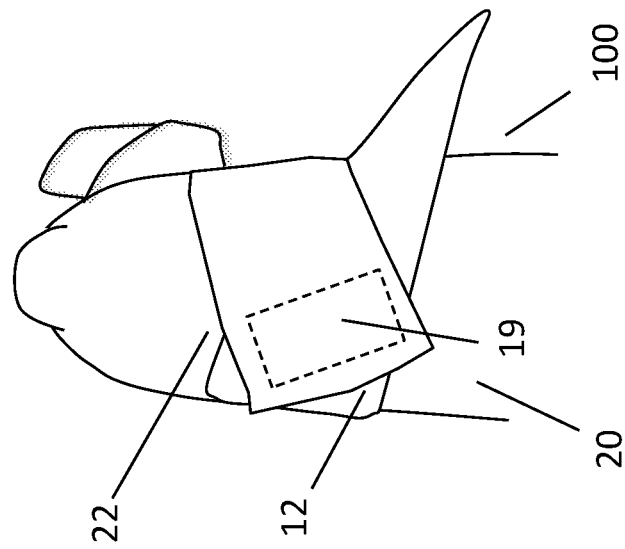
FIG. 2b illustrates wrapping a belt around a user's thigh and attaching the left end of the belt to the top of the thigh using a hook and loop fastener.

The wearable device described in the Incorporated Patent References containing a muscle contraction sensor may be placed against a muscle or muscle group being monitored and may be held against the muscle by a belt or strap. In this description, belt and strap may be used interchangeably. In this description, muscle engagement and muscle contraction may be used interchangeably. In this description, engagement and contraction may be used interchangeably with reference to a muscle engagement or muscle contraction. In this description, a muscle or muscle group may be referred to as a muscle. In an embodiment, muscle may refer to the core muscles. In this description, smart device may also include a dedicated device with a display, processor, wireless connectivity, and sound generator. The core muscles may include the transversus abdominus, inner obliques, outer obliques, rectus abdominus, longissimus, iliocostalis, multifidus, psoas, quadratus lumborum, pecs, diaphragm, and pelvic floor. In an embodiment, muscle may refer to another muscle or muscle group such as the gluteus maximus, gluteus medius, quadriceps, hamstrings, muscles of the forearm, muscles of the calf, latissimus dorsi, biceps, or triceps. In an embodiment, muscle may refer to another muscle of the body. In some applications, muscles not grouped with the core muscles in the list above may considered core muscles. In some applications, muscles grouped with the core muscles in the list above may not be considered core muscles.

With reference to FIG. 1a, a user 100 is shown wearing wearable device 10 on a belt 12 over the side 11 between the ribs and hip bone to monitor the core muscles 11. In an application, the belt 12 may be elastic or a portion of the belt may be elastic. Wearable device 10 is located on the inside of the belt with the muscle contraction sensor against the body. With reference to FIG. 1b, user 100 is shown wearing wearable device 10 to monitor the quadriceps 15. Wearable device 10 may be used to monitor both the core muscles 11 or the quadriceps 15. Wearable device 10 may also be used to monitor other muscles. With reference to FIG. 1c, an implementation of belt 12 for positioning wearable device 10 over the quadriceps 15 is shown. Belt 12 may be made of an elastic material like neoprene or a firm rubbery material. Belt 12 may utilize an attachment technology to support a firm fit around the body. For example, hook and loop fasters may be used. In an embodiment, magnets may be used. In the example shown in FIG. 1c, hook and loop fasters may be used. The outer side 18 of the belt may be covered with a material with hook qualities. This is commonly used in so-called neoprene slimming belts where a material with hook qualities is adhered to a thin layer of neoprene. A rectangle of with loop qualities 19 is attached to the inner side 13 of the belt. A number of attachment structures 14 to attach the wearable device 10 to the inner side 13 of the belt may be configured on the inner side 13 of the belt. In an embodiment, the attachment structure is a pocket 14 made of a soft yet strong material. By having several such pockets 14, the user may slide 16 wearable device 10 into a pocket 14 with a convenient location so that when the belt is placed over a body part such as the quadriceps 15, the patch of material with the loop qualities 17 can conveniently be placed onto the outer side 18 of the belt 12 with the device 10 in a desired position over the quadriceps 15.

Figure 2A:
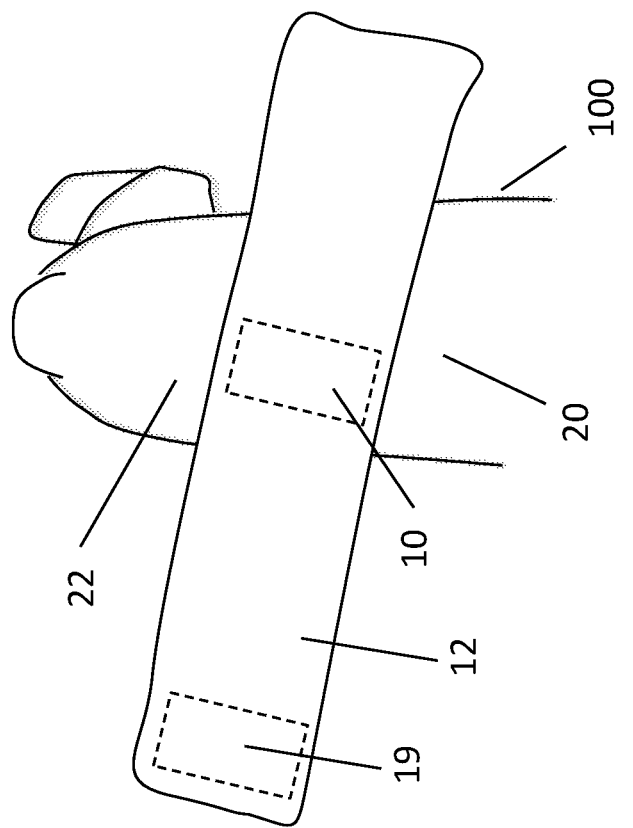
FIG. 2a illustrates an early step of positioning the belt of FIG. 1c over a user's quadriceps.

With reference to FIG. 2a. placement of the wearable device 10 over the right Vastis Medialis Obliques 22 (VMO) portion of the quadriceps is illustrated. A downward view of the right leg 20 while seated from the perspective of the user 100 is shown. Belt 12 from FIG. 1c is shown with the wearable device 10 in one of the pockets 14 and placed over the VMO 22. There is some excess belt on the right side of the leg that will not be used. On the left side of the leg, the portion of the belt with hook material 19 is shown facing downward. This part of the belt goes down, under, and around the right leg 20 and is pulled up over the right of the leg 20 and the hook material 19 is pressed onto the top of the belt 12 in the region over the wearable device 10. This may result in a firm fit of the belt 12 around the leg 20, with a good contact of the muscle contraction sensor on the wearable device 10 over the VMO 22. If the user 100 extends the right leg, this implementation of the belt may allow the firm fit of the belt around leg 20 to persist.

A number of sensor technologies may be utilized to detect the change in firmness of a muscle as the muscle transitions from relaxed to engaged, or engaged to relaxed. In an embodiment, the muscle contraction sensor may be sensitive to applied pressure or force. An implementation of a wearable device 10 utilizing a force-sensing resistor is described in the Incorporated Patent References. We repeat some material from the Incorporated Patent References for continuity of the current discussion. With reference to FIG. 3a, wearable device 10 is shown from a top view. The side of the wearable device that faces the body may have a slight curvature 34 and an extruding bumper 30. The extruding bumper is an element of the muscle contraction sensor. The area in the center of the device 32 behind the bumper 30 may contain the pressure sensor or force-sensing resistor, thus may require support in the housing to sustain a fair amount of pressure. The printed circuit board may reside in one of the side sections 33 and the battery may reside in the other side section 31. With reference to FIG. 3b, the face of the wearable device 10 is shown including the extruding portion of the bumper 30 and an outline of the frame 39 which may hold the bumper in place. There may be grips 37 on either side of the muscle contraction sensor to facilitate handling the wearable device. The cavities for the battery 31 and the printed circuit board 33 may be accessed from the back side of the device 35 and sealed with a cover (not shown).

Figure 4:
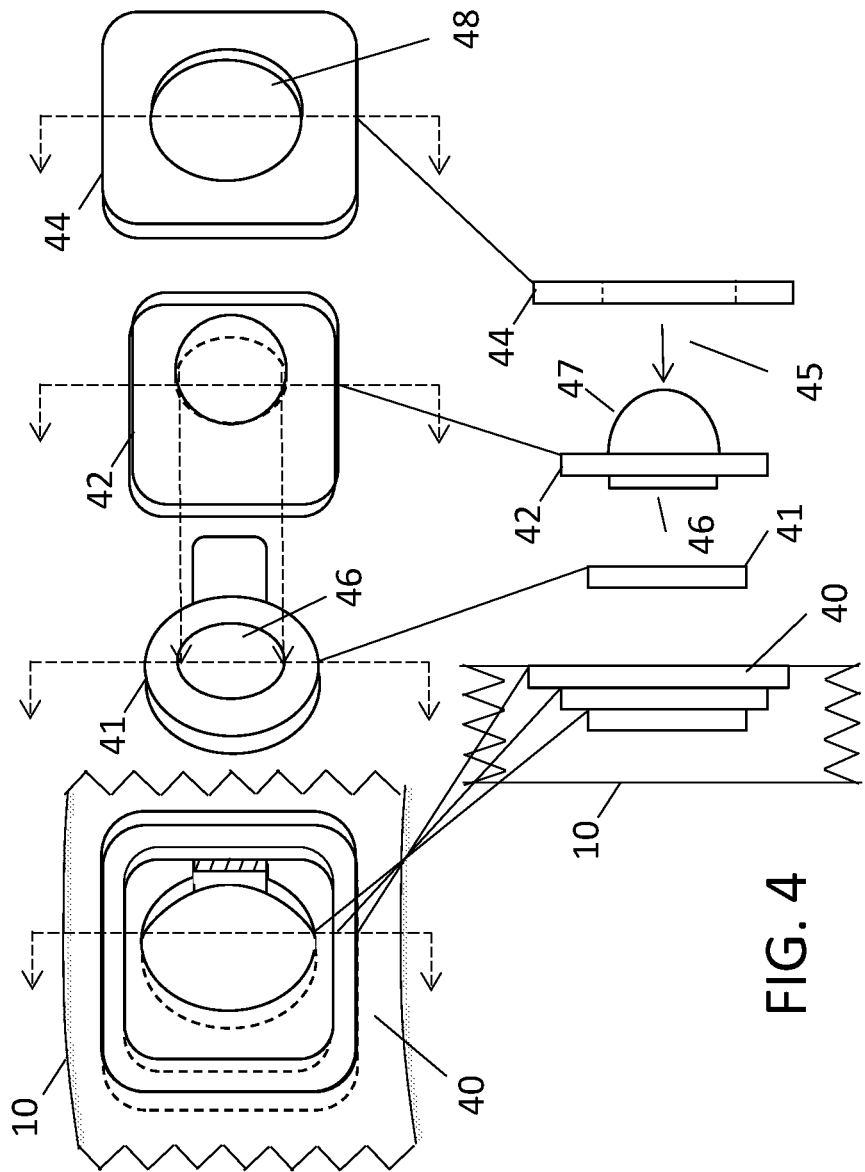
FIG. 4 illustrates a view a cavity in the device for housing the force-sensor, bumper, and frame where frame attaches to the device to hold the sensor and bumper in place.

With reference to FIG. 4, the housing in wearable device 10 may have a fitted cavity 40. The force-sensing resistor 41 may be placed first into the bottom of the cavity 40. Force-sensing resistor 40 may have active region 46. The bumper 42 may have a brim and a short cylinder 46 that may sit on active area 46 on its underside, and an elevated dome 47 on its topside. The bumper 42 may be made of a material with rubbery qualities. Frame 44 may have a round opening in its center 48 to allow the elevated dome 47 of the bumper 42 to extend outwards. Frame 44 may be larger than the brim of bumper 42 to hold the brim down. The frame 44 may be screwed on, glued, or use some other attachment method to secure the sensor 41 and bumper 42 into position. This design may enable the short cylinder 46 of the bumper 42 to freely displace downward into the force-sensing resistor 40 with a small amount of pressure 45 applied to the raised dome 47.

Figure 5:
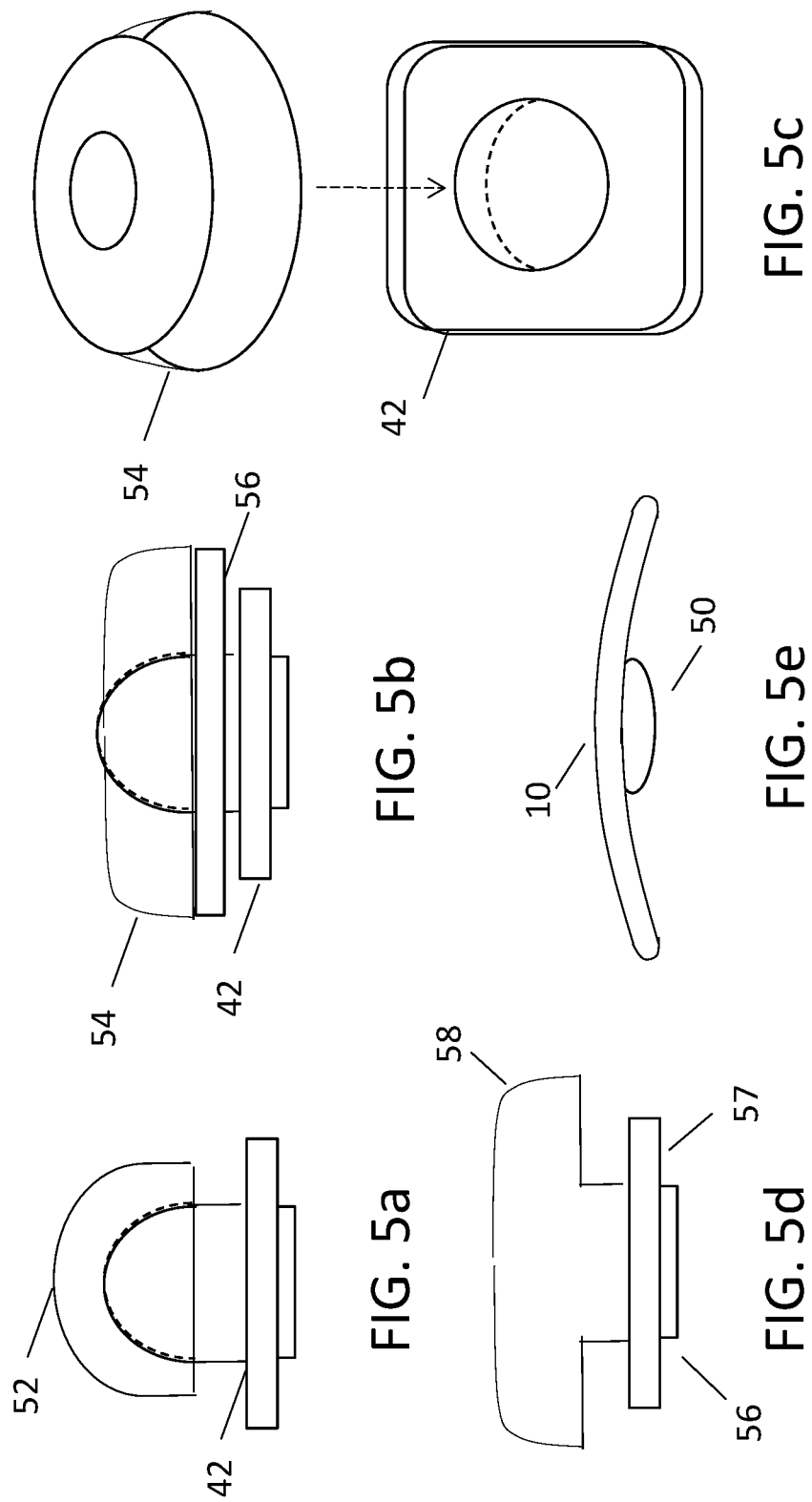
FIG. 5a-FIG. 5d illustrates different bumper and extender cap combinations.
FIG. 5e illustrates an abstraction of the wearable device with a muscle contraction sensor.

With reference to FIG. 5a, an extender cap 52 may be placed on the bumper 42. In an embodiment, extender cap 52 may be replaced by extender cap 54, illustrated in FIG. 5b, where extender cap 54 may have a different height and girth than extender cap 52. A different viewing perspective of bumper 42 and extender cap 54 is shown in FIG. 5c. In an embodiment, a flat ring 56 with a cutout to allow the bumper to protrude outwards may be placed around the bumper 42 on the face 34 of the wearable device 10. The flat ring 56 may keep the extender cap 54 from pressing down directly into the face of the wearable device 10 when pressure is placed on an outside edge of the extender cap 54, and reduce bending of the column region of the rubber bumper 42. In an embodiment, the ring 56 may be made from a firm pliable material such as felt, neoprene, or another material with similar properties.

Bumper 42 and extender cap 52 may together be referred to as a composite bumper. In an embodiment, the composite bumper functioning as a single element coupling the pressure or force sensor to the target muscle may be referred to as the bumper. The composite bumper may couple the pressure or force sensor 41 to the target muscle. With reference to FIG. 5d, the extender cap 52 may be combined into the bumper, resulting in a bumper with a larger head 56 for coupling directly to the target muscle. In an embodiment, bumper 56 may be manufactured with a rubber, silicone rubber, or similar material which would facilitate manufacturing a bumper with both a brim 57 and a large head 58. With reference to FIG. 5e, wearable device 10 may be abstracted to have a Muscle Contraction Sensor 50 which may include the bumper or composite bumper, the force-sensing resistor 41, and associated circuitry and structures.

When the user 100 engages the monitored muscle (the target muscle) from the relaxed state, the muscle under the Muscle Contraction Sensor 50 may firm. In addition, the portion of the body enclosed by the belt 12 may experience an increase in girth. These together may result in a greater pressure on the Muscle Contraction Sensor 50. When the user 100 relaxes the target muscle from the engaged state, the muscle under the Muscle Contraction Sensor 50 may soften. In addition, the portion of the body enclosed by the belt 12 may experience a decrease in girth. These together may result in a lesser pressure on the Muscle Contraction Sensor 50.

In an embodiment, the core muscles are engaged by firming the core musculature in the area surrounding the lumbar spine. This way of engaging the core may be referred to as abdominal bracing and may involve co-engaging a number of the muscles near and around the lumbar spine. In an embodiment, the core muscles may be engaged by pulling the naval toward the spine. This way of engaging the core may be referred to as abdominal hollowing and may mainly focus on engaging the transversus abdominus.

The Muscle Contraction Sensor 50 may be placed in a circuit to generate an output signal that is a monotonic function of the applied pressure on Muscle Contraction Sensor 50. In an embodiment, the circuit may be configured for the output signal to increase as the pressure on the Muscle Contraction Sensor 50 increases. In an embodiment, the circuit may be configured for the output signal to decrease as the pressure on the Muscle Contraction Sensor decreases. In the following, we will consider the configuration where the output signal increases as the pressure on the Muscle Contraction Sensor 50 increases. In an embodiment, the Muscle Contraction Sensor 50 may be implemented by a force-sensing resistor 41. In an embodiment, other sensors sensitive to applied pressure may be used. In an embodiment, a sensor sensitive to stretching may be used. In an embodiment, a strain gage sensor may be used.

Different sensing technologies may have characteristics and qualities that result in the need for different implementation requirements. While this description emphasizes the use of the force-sensing resistor, other technologies like the strain gage sensor, use of material sensitive to stretching, or other pressure or force sensing technologies may be utilized for the implementation of the Muscle Contraction Sensor 50. Common requirements for the different technologies may include: 1. Securing the sensor into the housing of the wearable device in a manner that will protect the sensor; 2. Providing a mechanism to couple the sensor to the target muscle effectively and with minimum sensitivity degradation; and 3. For some applications, having a provision to modify the coupling mechanism between the sensor and the target muscle for differences in user characteristics of the body region the target muscle resides, user comfort, and convenience for the user to make modifications.

Maximum voluntary contraction (MVC) may be a measure of the intensity with which a muscle is contracted. Surface EMG is sometimes used to measure MVC. EMG electrodes may be placed on a subject's muscle and the subject may be directed to contract the muscle to their firmest contraction intensity. An EMG reading may be taken to identify the amplitude of the electrical activity in the muscle. This EMG reading corresponding to the maximum contraction intensity may be referred to as 100% MVC or MVC. The subject may then perform exercises or a movement and the peak contraction intensity may be normalized to the MVC level. For example, if a subject subsequently contracts their muscle at half of 100% MVC, the muscle may be said to have contracted at 50% MVC.

Pressure may be used to identify a measure of muscle contraction intensity. When the target muscle is relaxed, there may be a non-zero baseline pressure on the Muscle Contraction Sensor. The system may arbitrarily define the muscle engagement value to be zero when the target muscle is relaxed. From this starting point, as user 100 engages the target muscle to the maximum intensity corresponding to 100% MVC, this may result in a maximum muscle engagement value measured by the wearable device 10 and app which may be identified as 100% maximum voluntary engagement or 100% MVE or MVE. When the target muscle is relaxed, the muscle engagement value may be zero and may be identified as 0% MVE.

If the relationship between the input pressure to the Muscle Contraction Sensor and the output to the Muscle Engagement Identification Algorithm is linear, then based on a reading of the muscle engagement value, a percent value of MVE may be determined. For example, when the target muscle is relaxed, the muscle engagement value may be zero. By way of example, suppose the muscle engagement value equals sixty (60) at 100% MVE. Then, if the engagement intensity of the target muscle is decreased and the muscle engagement value reduces to forty-five (45), the target muscle may be identified as being engaged to 75% MVE. MVE may not be an accurate estimate of MVC under all circumstances. But MVE may at least provide an estimate of muscle engagement intensity which may be useful for some applications.

In applications utilizing a force-sensing resistor 41 in the Muscle Contraction Sensor 50, the output signal may not be a linear function of the input pressure. For example, an embodiment may utilize a resistor divider circuit in which a linear resistor with a first terminal connected to system ground and a second terminal, the output of the circuit, connected to a first terminal of a force-sensing resistor 41 with the second terminal of the force-sensing resistor connected to Vsupply, a DC supply voltage. In an embodiment, the Vsupply may be 1.8V. In an embodiment, the Vsupply may be a voltage greater than or less than 1.8V. Using this circuit, the minimum output signal may be zero (0) volts and the maximum output signal may be Vsupply. As the input pressure is increased, the output signal may experience compression. Signal processing techniques may be used to linearize the output signal to compensate for compression.

Figure 6:
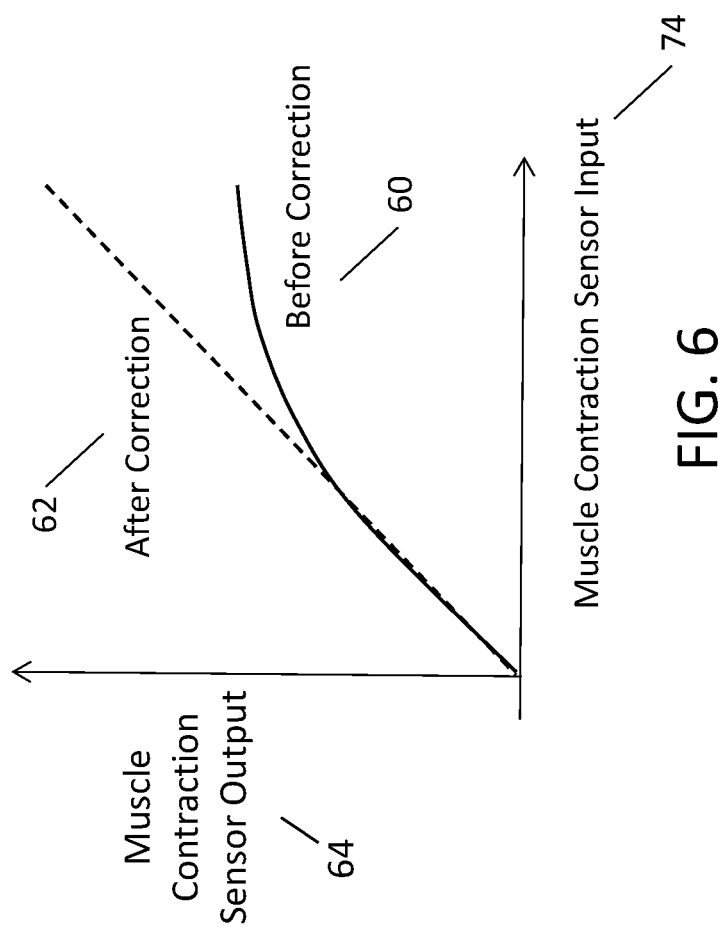
FIG. 6 illustrates the muscle contraction sensor output versus muscle contraction sensor input where the muscle contraction sensor output is a signal and the muscle contraction sensor input is a pressure. The muscle contraction sensor output is shown with compressive effects and after non-linearity compensation.

With reference to FIG. 6, the output of the Muscle Contraction Sensor Output 64 is plotted versus Muscle Contraction Sensor Input 74. Muscle Contraction Sensor Output 64 may be a voltage or current, or a digital representation of an output voltage or current. Muscle Contraction Sensor Input 74 may be an input pressure. The Muscle Contraction Sensor Output 64 depends on characteristics of the sensor technology, placement of the sensor into an electric circuit to generate a usable output signal, physical interface elements to couple the sensor to the target muscle, and may include other elements or components to make the sensing approach effective. The Muscle Contraction Sensor Output 64 versus Muscle Contraction Sensor Input 74 relationship may be non-linear. An illustrative example is shown in FIG. 6 where the signal before correction 60 is shown. While the input-output relationship appears linear at lower levels of input pressure, compression becomes evident at the higher input pressures in the signal before correction 60. Non-Linearity Compensation processing may correct the input-output relationship to be linear or improve the input-output relationship to be more linear. An example of the output after an ideal correction is shown in FIG. 6 as the signal after correction 62.

With reference to FIG. 7, a signal processing block diagram is shown for generating muscle engagement data for the muscle engagement identification algorithm and includes non-linearity compensation. Muscle Contraction Sensor Input (muscle pressure) 74 may be applied to the Muscle Contraction Sensor 50. The output 75 of the Muscle Contraction Sensor 50 may input the Non-Linearity Compensation 71 block. The Non-Linearity Compensation 71 block may correct for or reduce non-linearities introduced by the Muscle Contraction Sensor such as compression at higher values of input pressure. The output 76 of the Non-Linearity Compensation 71 block may input a Programmable Gain 72 block. The output of the Programmable Gain 72 block may be filtered by Filter 73 before becoming algInput 70, the Muscle Engagement Identification Algorithm input. The Filter 73 may provide low pass filtering and may use linear or non-linear filtering techniques. Parameters of the Non-Linearity Compensation 71 block and the Programmable Gain 72 block may be identified and stored during a factory calibration and stored in flash memory to calibrate part-to-part variations of the elements of the Muscle Contraction Sensor 50.

In an embodiment, the Non-Linearity Compensation 61 block may be implemented by a look-up table. A table containing input pressure and the corresponding output signal from the resistor divider circuit may be generated. The output signal comprises the first output. This first output may be used in a look-up-table to generate a second output where the first output is used as an index, and each possible value of the index has a corresponding output. In an embodiment, the look-up table may be designed to result in a relationship between input pressure and output of the look-up table that is substantially linear. In an embodiment, other methods for compensating for compression at larger input pressure levels may be used. In an embodiment, other methods for compensating non-linearity in the input-output transfer function of the Muscle Contraction Sensor 50 may be used.

At an appropriate location in the signal path from the Muscle Contraction Sensor 50 to the processor, conversion of the signal from an analog signal to a digital signal may occur to enable digital signal processing. In an embodiment of processing block diagram 79 in FIG. 7, this conversion may occur at Muscle Contraction Sensor 50 output 75. This may enable the Non-Linearity Compensation block 71 and the blocks shown to follow in the figure to be implemented using digital signal processing. Implementation of the analog-to-digital conversion may depend on the range and polarity of the source of the data signal. In the case of the implementation of the Muscle Contraction Sensor 50 utilizing the force-sensing resistor in a resistor divider, the output signal range may be from 0V up to Vsupply. An appropriate implementation of the analog-to-digital converter may have a minimum output of digital 0 (zero) with input voltage zero (0) volts, and maximum output of digital full-scale with input voltage Vsupply. The full-scale representation may depend on the number of bits in the analog-to-digital converter. With an 8-bit analog-to-digital converter, digital full-scale converted to decimal may be two-hundred fifty-five (255). With a 10-bit analog-to-digital converter, digital full-scale converted to decimal may be one-thousand twenty-three (1023).

Figure 8B:
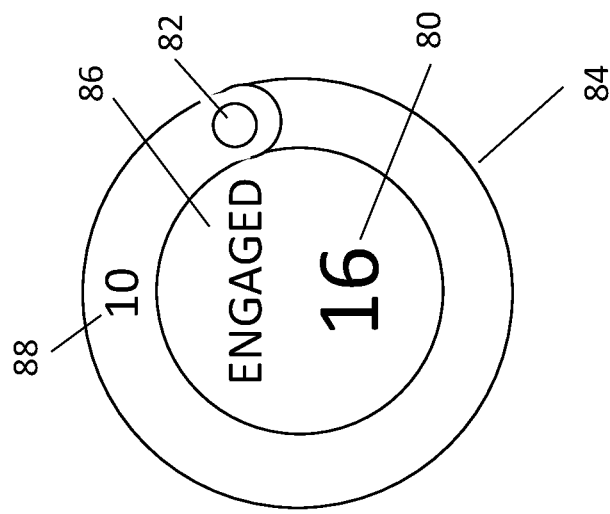
FIG. 8b illustrates a muscle engage circle with the muscle engaged.
Figure 8A:
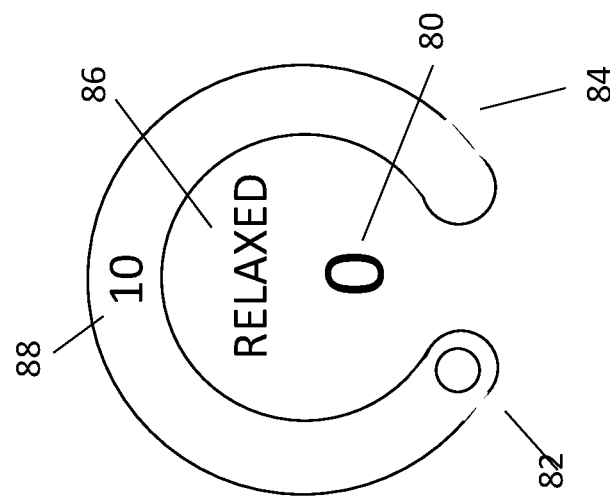
FIG. 8a illustrates a muscle engage circle with the muscle relaxed.

With reference to FIG. 8a, an example display structure showing data the app may report to a user is shown. Let us refer to this structure as a Muscle Engage Circle 84. The Muscle Engage Circle 84 has a Muscle Marker 82 which reflects the value of the Muscle Engaged Value 80. The Muscle Engaged Value 80 is the output of the Muscle Engagement Identification Algorithm. The engageThreshold 88 is shown on the top center of the Muscle Engage Circle 84. In this example, the engageThreshold 88 has a value of ten (10). The Muscle Status 86 indicates if a target muscle is relaxed or engaged. When the Muscle Engaged Value 80 equals or exceeds the engageThreshold 88, the target muscle may be identified as engaged. With reference to FIG. 8b, the effect of the Muscle Engaged Value 80 increasing to a value of sixteen (16) is shown. This increase in the Muscle Engaged Value 80 may result in the Muscle Marker 82 rotating clockwise around the Muscle Engage Circle 84. Since the Muscle Engaged Value 80 exceeds the engageThreshold 88, the Muscle Status 86 changed to engaged. Another feedback element indicating the Muscle Status 86 changing to engaged may include the Muscle Engage Circle 84 becoming a continuous circle.

Two critical system status elements communicated from the Muscle Engagement Identification Algorithm via the app may include the Muscle Status 86 and the Muscle Engaged Value 80. Different display structures may be used to communicate the Muscle Status 86 and the Muscle Engaged Value 80. In some applications, the engageThreshold 88 may also be communicated. Different display elements may utilize other design elements to communicate the Muscle Status 86 and the Muscle Engaged Value 80 and changes in the Muscle Status 86 and the Muscle Engaged Value 80.

In an embodiment of the present system, the input from the analog-to-digital converter may be unipolar and range from digital zero (0) to digital full-scale. Whereas Muscle Engaged Value 80 may have a digital representation that may be bipolar, with a nominal value of zero and range from negative to positive values. In an embodiment, the unipolar to bipolar conversion may occur as follows. Let diffInput[n]=algInput[n]−algInput [n−1] where diffInput[n] is difference input at time index n, algInput[n] is algInput a time index n, and algInput[n−1] is algInput at time index n−1. Let musEngValue[n]=musEngValue[n−1]+diffInput[n] where musEngValue[n] is Muscle Engaged Value 80 at time index n and musEngValue[n−1] is Muscle Engaged Value 80 at time index n−1. Signal musEngValue[n] is the current value of Muscle Engaged Value 80. This may provide a unipolar to bipolar conversion. With the target muscle relaxed, the system may require a reset to initialize musEngValue[n] (Muscle Engaged Value 80) to zero (0). In an embodiment, another approach for the analog-to-digital conversion and signal representations and conversion between signal representations may be utilized.

With reference to FIG. 8c, an embodiment of a display structure utilizing a myokinesiograph 860 in the app running on the smart device is shown. The myokinesiograph 860 is a graph for displaying muscle (myo) data, movement (kinesio) data, raw sensor data, thresholds, parameter status, and feedback over time 149. In an embodiment, other data, instruction, and information relevant to the application or useful to the user 100 may be displayed in the myokinesiograph 860. Horizontal grid lines 801 that facilitate estimating instantaneous and past values of data may be displayed in the myokinesiograph 860. Other applications of the myokinesiograph 860 will subsequently be described. The Muscle Engaged Value 80 is shown on the myokinesiograph 860 as Muscle Engaged Value 800. The engageThreshold 88 is shown on the myokinesiograph 860 as engageThreshold 880. With reference to FIG. 8d, a myokinesiograph 860 is shown where the Muscle Engaged Value 800 has increased above engageThreshold 880. The Muscle Status 86 is shown with a different indication of line type. In FIG. 8c, the target muscle is relaxed and the Muscle Engaged Value 800 is shown as a solid line. In FIG. 8d, the target muscle is engaged and the Muscle Engaged Value 800 is shown as a dashed line. In an embodiment, other graphing changes may be made to the Muscle Engaged Value graph line 800 when the Muscle Status 86 changes between relaxed and engaged. In an embodiment, line colors may change. In an embodiment, line thickness may change. In an embodiment, shading under the line may change in color or opacity. In an embodiment, Muscle Status 860 may be presented graphically and visually in ways other than already described.

With reference to FIG. 8e, movement data 820 is graphed together with Muscle Engaged Value 800. This may facilitate viewing the timing relationship between movements and engagement of the target muscle. Data from the movement sensors may be viewed independently or combined in ways relevant to the selections of the user. For example, data from a three dimensional gyro may be used for display. In an embodiment, the user 100 may select to view data from one of the gyros at a time simultaneously with muscle engagement data from the target muscle. In an embodiment, the user 100 may view data from more than one of the gyros at a time simultaneously with muscle engagement data from the target muscle. In an embodiment, the user may select the Any Gyro mode. In the Any Gyro mode, data from available gyros are analyzed. In an embodiment utilizing Any Gyro mode with a three-axis gyro, the algorithm may track the magnitude of all three gyros and select to graph data from the gyro with data first exceeding a threshold. Any Gyro mode may be useful in applications where a user 100 is practicing engaging their core before and through a variety of different movements or performing an exercise movement. In an embodiment in which the Any Gyro mode is being utilized, a new gyro selection may be made each time the target muscle transitions from relaxed to engaged. In an embodiment in which the Any Gyro mode is being utilized, a new gyro selection may be made while the target muscle remains engaged.

In applications where timing between engaging a target muscle like the core before and through a movement is being evaluated, it may be beneficial to convert the movement data from the raw 'analog' signal data to a 'movement' signal data. For example, when the sensor is a gyro, the gyro data may be converted into movement data which may be rotation. In the example of gyro data 820 as shown in FIG. 8e, gyro data 820 is proportional to the instantaneous angular velocity about an axis. In FIG. 8f, gyro data 820 from FIG. 8f is replotted as rotation signal 830 with a value of +15 if the raw gyro data exceeds or is equal to +10, a value of −15 if the raw gyro data is less than or equal to −10, and a value of zero if the magnitude of the raw gyro data is less than 10. Rotation signal values of +15 and −15 may be unit-less and chosen arbitrarily. In an embodiment, a simplifying abstraction may be utilized where rotation signal 830 may identify a rotation about an axis when the angular velocity equals or exceeds a threshold; conversely, rotation signal 830 may identify no rotation when the angular velocity is less than a threshold. In an embodiment, the simplifying abstraction may further identify the polarity of rotation. A more rigorous analysis may convert angular velocity into rotation, in radians, by integrating angular velocity. Such analyses may be cumbersome, for example, the more accurate analysis may introduce the need to calibrate for the effects of offsets, gain errors, and drift associated with low-cost sensors. And while introducing new computational challenges and the potential requirement for calibrations, the benefits from higher accuracy through more accurate computations may be inconsequential for many applications.

With reference to FIG. 8g and FIG. 8h, two graphs are shown. The first graph in FIG. 8g shows a relatively small time difference 840 between the target muscle engaging and the start of the body rotation. The second graph in FIG. 8h shows a larger time difference 840 between the target muscle engaging and the start of the body rotation. In an embodiment, if time difference 840 is less than the Engage-to-Move Delay, then the movement may be considered an unprotected qualifying movement or an unprotected movement. If the time difference 840 equals or is greater than the Engage-to-Move Delay, the movement may be considered a protected qualifying movement or a protected movement. A protected movement may be one which is supported by a target muscle whereas an unprotected movement may be one which is not supported or not adequately supported by a target muscle. In an embodiment, the Engage-to-Move Delay may be 250 msec. The app may provide visual feedback via display colors, line shading, flashing elements, pop up elements, or may use other methods of visual feedback together with audio feedback to communicate that a movement was a protected or unprotected movement to the user 100. In an embodiment, only protected movements may be identified with feedback. In an embodiment, only unprotected movements may be identified with feedback. In an embodiment, both protected and unprotected movements may be identified with feedback.

FIGS. 8c through 8h and the accompanying describes describe capabilities of the Myokinesiometer, a tool for acquiring and displaying muscle data and movement data simultaneously for muscle training and muscle retraining, effective exercising, and motor skill or procedural memory development. The myokinesiometer may include the wearable device 10 and the myokinesiograph 860 and may be used for displaying, selecting, measuring, and reporting on muscle and movement data. The myokinesiometer may provide insights into protected and unprotected qualifying movements for therapy, body mechanics for injury reduction, athletic performance improvement, and other applications in which engaging the core before and through a movement may be beneficial or engaging another target muscle before and through a movement may be beneficial. The myokinesiometer may be used to measure timing relationships between muscle engaging and specific body movements, observe muscle intensity degradation with time as a muscle fatigues during an exercise rep or throughout an exercise session, and continuity of muscle engagement throughout a movement. The myokinesiometer may be used for additional applications and to provide additional insights to a user, therapist, trainer, or coach to improve exercise effectiveness. The visual feedback of the display in the myokinesiometer may be complemented with sounds provided by the app and buzzing provided by the wearable device 10.

In an embodiment, the myokinesiometer may provide display and audio feedback, and buzzing within the wearable device to identify protected or unprotected qualifying movements, or protected or unprotected movements. In an embodiment, the myokinesiometer may measure time between events such as a target muscle engaging and a body rotation. In an embodiment, the myokinesiometer may allow the user to select a beginning or end of a rotation, or evaluate a second rotation and ignore a first rotation. In an embodiment, the myokinesiometer may allow the user to select, evaluate, and measure different characteristics and timing relationships between a target muscle engagement and specific aspects of body rotations, body movements, body orientations, or body elevations. In an embodiment, rotation, orientation, and elevation may be analyzed depending on available sensors in the wearable device.

Returning to the example described with reference to FIG. 8g and FIG. 8h, timing analysis was performed using the start of engagement of the target muscle and the start of a body movement. The myokinesiometer may perform timing analyses on other specific aspects of movements. Many movements in everyday life and athletics contain two rotations. For example, standing up from the seated position (sit-to-stand) may involve: 1. Leaning forward and lifting the body off the seat; and 2. Leaning back to straighten during to movement up to stand. Jumping may involve two rotations: 1. Leaning forward as the subject bends their knees; and 2. Leaning back as the legs spring the subject into the air and the subject straightens to achieve maximum height.

With reference to FIG. 8*i*, an example of the core muscles being the target muscle and gyro data providing movement data will be described. Converting gyro data from the raw analog data to rotation data may facilitate its use for timing analyses: 1. Rotate forward (if gyro data positive and greater than or equal the gyroThreshold); 2. Rotating back (if gyro data is negative and less than or equal −gyroThreshold); and 3. Not rotating (if gyro data magnitude is less than gyroThreshold). In FIG. 8*i*, the core is shown engaged before and throughout two body rotations as Muscle Engaged Data is graphed 800 showing a Muscle Engaged Value 80 starting from zero and transitioning to approximately forty-seven (47) before and through two rotations before returning to zero. In the sit-to-stand example, it may be desirable in an application for the user 100 to engage their core before and through the entire movement. Graphed rotation data 411 shows a first rotation corresponding to the user 100 leaning forward and lifting their body off the seat, and a second rotation corresponding to the user 100 leaning back to straighten during to movement up to stand. In this example, a protected movement may be defined by the core being engaged prior to edge A 840, the first edge of the first rotation, through edge D 843, the second edge of the second rotation. The user 100 may select which of the four edges the target muscle should be engaged before in order to meet the requirement for engaging using a pop up table in the app 886 shown in FIG. 8*j*. The user 100 may select which of the four edges the target muscle should be engaged after in order to meet the requirement for relaxing using a pop up table in the app 887 shown in FIG. 8*k*. An option in FIG. 8*k* is none. If this is selected, the target muscle may be relaxed following the edge selected for engaging. In an embodiment, when the target muscle is relaxed and the myokinesiograph 860 is touched, the myokinesiograph 860 may be paused and UI table options such as those presented in FIG. 8*j* and FIG. 8*k* may become available to the user.

Returning to the jumping example, in an application, it may be desirable for the user 100 to engage their core prior to the start of the second rotation, as the user leans back as their legs spring them up into the air. A firm core prior to and during the spring upwards may be beneficial for improving jump performance and may be beneficial for low back support. For some applications, it may be desirable for the user to keep their core engaged through after the end of the second rotation. In this example, a protected movement may be defined by the core being engaged prior to edge C 842, the first edge of the second rotation, through edge D 843, the second edge of the second rotation. These selections may be made easily using the described graphical user interface.

These examples may illustrate the simplicity for evaluating different types of protected and unprotected qualifying movements and protected and unprotected movements using the myokinesiometer.

In an embodiment, the myokinesiograph may simultaneously be displayed with an instructional video to enable the user's target muscle and movement data to be displayed while the user 100 follows instruction. In an embodiment, said instructional video content may be streamed from the Internet. In an embodiment, said instructional video content may be available from the app. In an embodiment, the myokinesiograph may simultaneously be displayed with audio instruction to enable the user's target muscle and movement data to be displayed while the user 100 follows instruction. In an embodiment, instructional content may be provided from a web app. In an embodiment, the myokinesiograph may simultaneously be displayed with a live video feed of the user 100. In an embodiment, said live video feed and myokinesiograph may be recorded for a video recording of the user performing a movement or exercise with the data displayed by the myokinesiograph. Said recording may be beneficial to record performance or to be used in instruction. In an embodiment, the myokinesiograph may include more than one graph, allowing a first data to be graphed in one graph and a second data to simultaneously be graphed in a second graph. In an embodiment, if the target muscle is not engaged and the myokinesiograph 860 is touched, the myokinesiograph 860 may be paused, and may further enable the user to utilize gesture driven commands on the myokinesiograph 860. In an embodiment, gesture driven commands on the myokinesiograph 860 may include zooming in and out, identifying points on the graphed data to use for measurements, and other user interface (UI) applications.

In an embodiment, the myokinesiometer may be used to record video or sound of a user 100 performing a movement or movement sequence together with simultaneous user data displayed in the myokinesiograph that may benefit an objective in a therapy rehab, injury reduction, performance improvement, or other tangible exercise objective.

The evaluation of protected and unprotected qualifying movements and protected and unprotected movements may include feedback on the beginning side of the muscle contraction and on the end side of the muscle contraction. In an embodiment, the app may provide an first audible beep when the target muscle is engaged, a second audible beep when the first protected movement is identified. In an embodiment, the app may provide a third audible beep when the second protected movement is identified. In an embodiment, the app may provide no beep if a second protected movement is identified but an audible error buzz in the app if the second movement is not protected. In an embodiment, other combinations of feedback, both audible and visual may be used. In an embodiment, different beep sounds may be used for the first, second, and third beeps.

Figure 9:
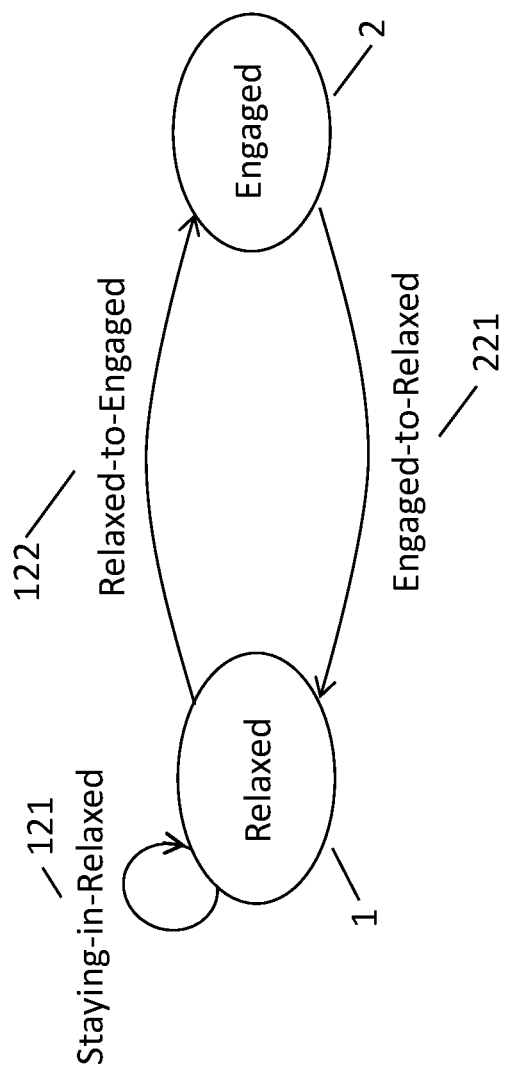
FIG. 9 illustrates a state diagram for the muscle engagement identification algorithm.

In an embodiment, the Muscle Engagement Identification Algorithm (Algorithm) may contain two states as shown in FIG. 9:

Relaxed 1—the target muscle is identified as relaxed; and

Engaged 2—the target muscle is identified as engaged.

In Relaxed 1, the target muscle is identified as relaxed and in Engaged 2, the target muscle is identified as engaged. In normal operation, the system transitions between Relaxed 1 and Engaged 2 via the Relaxed-to-Engaged 122 state transition when the target muscle begins relaxed and the user 100 engages the target muscle. The system transitions between Engaged 2 and Relaxed 1 via the Engaged-to-Relaxed 221 state transition when the target muscle begins engaged and the user 100 relaxes the target muscle. As will be described, there may be more than one trigger for the Relaxed-to-Engaged 122 transition and more than one trigger for the Engaged-to-Relaxed 221 transition. In an embodiment, the Muscle Engaged Value 80 may be initialized or reset on each Engaged-to-Relaxed 221 transition. In an embodiment, the Muscle Engaged Value may be initialized or reset on a specific Engaged-to-Relaxed 221 trigger but not every Engaged-to-Relaxed 221 trigger. In an embodiment, the value the Muscle Engaged Value 80 may be initialized or reset to may be zero (0).

Let us consider an application in which the Muscle Engagement Identification Algorithm is processing abdominal bracing with a Muscle Contraction Sensor 50 configuration where the output signal of the Muscle Contraction Sensor 50 increases with increasing input pressure. A number of design elements may be used in the Muscle Engagement Identification Algorithm to distinguish between a target muscle being engaged or relaxed.

Reset Transition 021

The core may be identified as engaged and the Algorithm in Engaged 2 while the target muscle is actually relaxed. The system may persist indefinitely in this erroneous condition without an intervention. One way the system may be in Engaged 2 while the target muscle is relaxed is associated with startup. When the wearable device 10 is first placed on over the target muscle and the pressure on the Muscle Contraction Sensor transitions from a low value to a baseline value, the increase in pressure may be identified as an engagement of the target muscle. A second way the system may be in Engaged 2 while the target muscle is relaxed is during normal operation when body movements cause unexpected changes in pressure patterns on the Muscle Contraction Sensor 50. A third way the system may be in Engaged 2 while the target muscle is relaxed is when muscle engagement patterns cause unexpected changes in pressure patterns on the Muscle Contraction Sensor 50. There may be other ways the system may be in Engaged 2 while the target muscle is relaxed.

An intervention that may result in a transition from state Engaged 2 while the target muscle is relaxed to state Relaxed 1 is a Reset 021. There are a number of interventions that may trigger a Reset 021. With reference to FIG. 10a, in an embodiment, the wearable device 10 may have a button or the app scene on the smart device may have a button or other distinguishable display feature for triggering a Reset 021. If there is a button on the wearable device 10 for triggering a Reset 021 and if the button is pushed, or if there is a button or other distinguishable feature on the app scene for triggering a Reset 021, and if it is touched, a Reset 021 may be triggered. In an embodiment utilizing a Muscle Engage Circle 84, the distinguishable feature on the app may be the circle itself. In said embodiment, touching the Muscle Engage Circle 84 may trigger a Reset 021. In an embodiment, another feature in the app may be used to trigger a Reset 021. In an embodiment of a scene that utilizes a myokinesiograph 860, if the target muscle is engaged and the myokinesiograph 860 is touched, a Reset 021 may be triggered; if the target muscle is not engaged and the myokinesiograph 860 is touched, the myokinesiograph 860 may be paused, and may further enable the user to utilize gesture driven commands on the myokinesiograph 860. In an embodiment, when the myokinesiograph 860 is paused, the current data is held and displayed, and no new data is added to the graph.

Figure 10C:
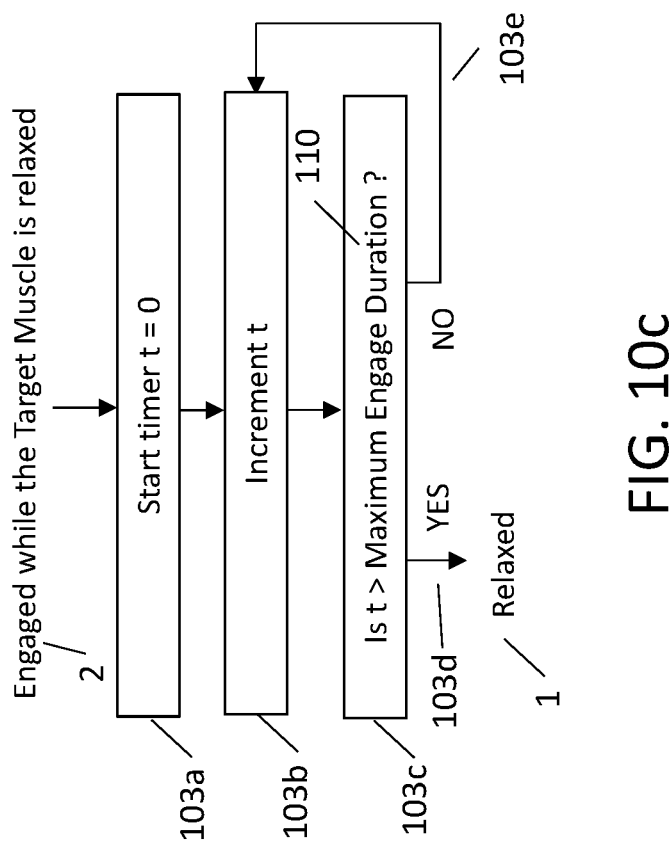
FIG. 10a-FIG. 10c signal flow diagrams for embodiments to reset the muscle engagement identification algorithm from an initial or stuck state where the target muscle is relaxed while the algorithm is in the engaged state to one of the two desired states.
Figure 10A:
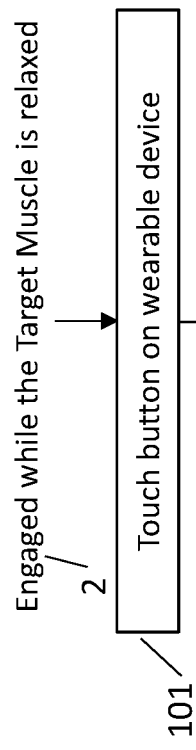
Figure 10B:
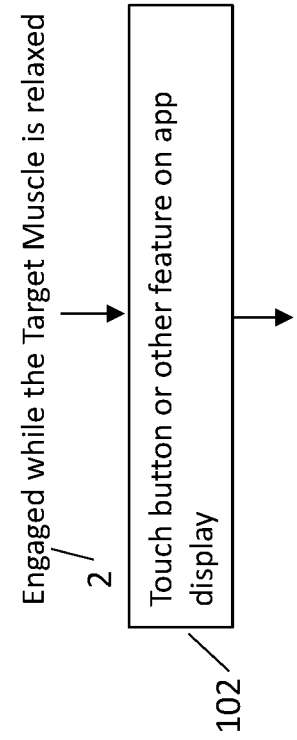

With reference to FIG. 10c, in an embodiment, a control parameter Maximum Engage Duration 110 period of time may be defined. If the system is in Engaged 2 while the target muscle is relaxed for the Maximum Engage Duration 110, the Muscle Engagement Identification Algorithm may trigger a Reset 021. In an embodiment, the Maximum Engage Duration 110 may be four (4) seconds. In an embodiment, the Maximum Engage Duration 110 may be user programmable.

In an embodiment, the user 100 may trigger a Reset 021 by physically manipulating the wearable device 10 in a manner that is detectable by one or more sensors on the wearable device 10 and identifiable by the Muscle Engagement Identification Algorithm. In an embodiment, the reset movement for the wearable device 10 may be defined such that the reset movement is unlikely to occur in normal operation. With reference to FIG. 11a and FIG. 11b, a side view of the wearable device 10 is shown in both figures. In FIG. 11a, angle 111 is shown to be a reference angle of 90 degrees. In FIG. 11b, the wearable device 10 is quickly pushed and then released by the user's fingers, causing the wearable device 10 to rotate a small amount. This rotation causes angle 111 to increase to 90+β degrees on the push and return to 90 degrees on the release. The result may be a short series of impulses that may be detected by the gyro monitoring x-axis rotation as defined in FIG. 11c. The impulses from the gyro may be input to a signal processing block which may distinguish this reset movement from other movements.

With reference to FIG. 11d, an embodiment of a signal processing block to distinguish the reset movement is shown. The Gyro Output 114 may first enter a high pass filter 115, followed by a non-linearity 116, followed by a lowpass filter 117, and finally followed by a slicer 118 to generate the Reset Signal 119 which may trigger Reset 021. The high pass filter 115 may be designed to pass changes in rotation that occur as the user is pressing and releasing wearable device 10. In an embodiment, the non-linearity 116 may be an absolute value function. In an embodiment, the non-linearity block 116 may implement a squaring function. In an embodiment, the non-linearity block may be implemented using another approach. The output of the non-linearity block 116 enters the low-pass filter 115 which passes the envelope of the output of the non-linearity block 116. The slicer 118 identifies when the sequence of impulses is adequate to build an envelope of sufficient magnitude to result in a Reset Signal 119 which may trigger Reset 021. In an embodiment, the signal processing block shown in FIG. 10d may be designed so that when the user 100 presses and releases the wearable device at a frequency of approximately 6 Hz, Reset 021 is triggered in approximately one-half second. In an embodiment, the parameters of the signal processing block of FIG. 10d may be optimized for a different frequency of press-release for a different duration of time. In an embodiment, a different sensor may be used. In an embodiment, a different algorithm for identifying a Reset 021 may be used.

Other implementations of wearable device 10 movement together with a signal processing implementation to identify resulting signal patters from one or more sensors may be used to trigger a Reset 021. Important attributes of an implementation include: movements are readily identifiable by a signal processing block; movements are simple for the user 100 to perform; and the movements results in movements of the wearable device 10 that may be different from movements that may occur in normal operation including active aerobic exercising.

Staying-in-Relaxed 121

Staying-In-Relaxed 121 is not a transition from one state to another. Instead it may include actions the system may take to maintain the system in state Relaxed 1 and in a condition prepared to respond to changes in target muscle firmness. Staying-In-Relaxed 121 may persist while the Muscle Engaged Value 80 is less than the engageThreshold 88.

When the target muscle is relaxed and the user 100 moves, pressure on the Muscle Contraction Sensor 50 may change and the Muscle Engaged Value 80 may increase by an amount less than the engageThreshold 88 or the Muscle Engaged Value 80 may decrease. Staying-In-Relaxed 121 may maintain the Muscle Engaged Value 80 near a value of zero. With reference to FIG. 12*a*, in an embodiment, if the Muscle Engaged Value 80 is non-zero and stays constant for a control parameter Relaxed Movement Idle Period 126 period of time, the Muscle Engaged Value 80 may be reset to zero. In an embodiment, the Relaxed Movement Idle Period 126 may be four (4) seconds. With reference to FIG. 12*b*, in an embodiment, when the Muscle Engaged Value 80 is non-zero, periodically at the control parameter Relaxed Leak Interval 128 period of time, the Muscle Engaged Value 80 may leak toward zero. For example, the Relaxed Leak Interval 128 may be one (1) sec. In this case, the magnitude of the Muscle Engaged Value 80 may be decreased every one (1) sec. With reference to FIG. 12*c*, in an embodiment, if the Muscle Engaged Value 80 decreases below the control parameter Relaxed Minimum Value, the Muscle Engaged Value 80 may be kept at the Relaxed Minimum Value. In an embodiment, the Relaxed Minimum Value may be zero. Other algorithms may be utilized to implement Staying-In-Relaxed 121 to keep the system prepared to respond in a repeatable manner to an increase in the pressure on the Muscle Contraction Sensor 50. Different approaches to implement Staying-In-Relaxed 121 may be used in isolation or in different combinations. In an embodiment, a technique to implement Staying-In-Relaxed 121 may be turned on or off by the user 100. In an embodiment, control parameters for approaches to implement Staying-In-Relaxed 121 may be programmed by the user 100. In embodiment, an approach to implement Staying-In-Relaxed 121 and associated control parameters may be controlled by the app for a specific application.

Relaxed-to-Engaged State Transition 122

When the user's muscle begins to engage, pressure on the Muscle Contraction Sensor 50 may begin to increase and the Muscle Engaged Value 80 may being to increase. In an embodiment, Relaxed-to-Engaged 122 from state Relaxed 1 to state Engaged 2 may be triggered by one of a multiplicity of events. In an embodiment, the Relaxed-to-Engaged 122 may have additional qualifiers to increase confidence that the target muscle has engaged.

With reference to FIG. 13*a*, in an embodiment, a trigger for Relaxed-to-Engaged 122 occurs when the Muscle Engaged Value 80 equals or exceeds the engageThreshold 88.

In some applications, it may be desirable to qualify the muscle engagement and provide feedback only for muscle engagements lasting a minimum amount of time. The tradeoff may be delay in the provision of feedback. In an embodiment, the Muscle Engaged Value 80 must additionally maintain a value equal to or greater than the engageThreshold 88 for a control parameter Minimum Engaged Duration 132*i* period of time. In an embodiment, the Minimum Engaged Duration 132*i* may equal one (1) second. In an embodiment, the Minimum Engaged Duration 132*i* may have a value less than one (1) second. In an embodiment, Minimum Engaged Duration 132*i* may have a value greater than one (1) second. With reference to FIG. 13*b*, beginning in Relaxed 1, when the Muscle Engaged Value 80 equals or exceeds the engageThreshold 88 a timer is started 132*b*. When the timer exceeds the Minimum Engage Duration 132*i*, Relaxed-to-Engaged 122 is triggered, and the system enters Engaged 2.

In some applications, it may be desirable to have the user 100 hold off on all movement prior to engaging the target muscle in order to engage the muscle in isolation from other muscles and body movements. This may facilitate neural patterning and motor skill development. In an embodiment, when the Muscle Engaged Value 80 equals or exceeds the engageThreshold 88, the Muscle Engagement Identification Algorithm evaluates if data from the movement sensors indicates movement greater than a nominal threshold at the time the Muscle Engaged Value 80 equals or exceeds the engageThreshold 88. With reference to FIG. 13*c*, beginning in the Relaxed 1, when the Muscle Engaged Value 80 equals or exceeds the engageThreshold 88, movement sensor data may be evaluated to identify movement above a nominal threshold. If no appreciable movement is detected 133*c* (sensor data indicates movement less than the nominal threshold), Relaxed-to-Engaged 122 may be triggered, and the system may enter Engaged 2. If appreciable movement is detected 133*d*, the system may remain in Relaxed 1.

For some applications, it may be desirable for a user 100 to engage the target muscle, then pause momentarily before moving in order to enhance neural muscular training. With reference to FIG. 13*d*, beginning in Relaxed 1, when the Muscle Engaged Value 80 equals or exceeds the engageThreshold 88, movement sensor data may be evaluated to identify movement above a nominal threshold for a period of a Movement Free Time. If no substantial movement is detected 134*c* during the Moment Free Time, Relaxed-to-Engaged 122 may be triggered, and the system may enter Engaged 2. If appreciable movement is detected 134*d* during the Movement Free Time, the system may remain in Relaxed 1. Returning to FIG. 8*h*, the time between engaging the target muscle and the first edge of the first rotation 840 must exceed the Movement Free Time in order for Relaxed-to-Engaged 122 to be triggered. This timing requirement may be easily displayed as shown in FIG. 8*h* by the myokinesiometer 860.

In an application where the target muscle is the core muscles, when the user 100 takes a deep breath in, the pressure on the Muscle Contraction Sensor 50 may increase and the Muscle Engaged Value 80 may exceed the engageThreshold 88. This may trigger a false positive identification of an engaged core, though the user 100 may consider their core relaxed. In an embodiment, a trigger may be established for Relaxed-to-Engaged 122 to differentiate between a user 100 engaging their core and a user taking a breath in. In an embodiment, this trigger may be selected as an alternative to the simple trigger described with reference to FIG. 13*a*. In addition to utilizing the engageThreshold 88, this trigger may utilize additional characteristics of the Muscle Engaged Value 80 to identify a Relaxed-to-Engaged 122 trigger.

With reference to FIG. 14*a* and FIG. 14*b*, illustrative examples of signal algInput 70 the Muscle Engagement Identification Algorithm input is shown over time 149. Signal algInput 70 may be proportional to the Muscle Contraction Sensor Input 65. In FIG. 14*a*, the algInput 70 for a cycle of engage-relax 146 is shown. Signal algInput 70 may begin low 141*c* with the core relaxed, increases as the core engages 141*a*, stays relatively constant while engaged 142, decreases as the core is relaxed 141*b*, and remains low as the core is relaxed 141*d*. In FIG. 14*b*, the pressure for a breathing cycle (breath in-breath out) 148 of belly breathing is shown. Belly breathing may cause the abdominal section to expand as the user 100 inhales and compress as the user 100 exhales. A similar breathing response may occur for breathing approaches other than belly breathing. Signal algInput 70 may begin low 143*c* with a relaxed core, increases as the user 100 inhales 143*a*, may stay constant for a short period of time 144, decreases as the user 100 exhales 143*b*, and again remains low as the core is relaxed 143*d*. When most people inhale, signal algInput 70 may increase more slowly than when they engage their core. This is indicated by the relatively smaller slope of algInput 70 during inhale 143*a* compared with engage 141*a*. This difference in slope may be used to distinguish between an inhale 143*a* and a core engage 141*a*, and may result in fewer false positive identifications of core engage that may otherwise be triggered when the user 100 inhales during a breath. With practice utilizing the trigger that will be described next, some users may develop a quicker core engage and a slower inhale to further reduce the likelihood of core engage identification errors.

Referring to FIG. 15*a* and FIG. 15*b*, signal algInput 70 is shown for two cases. In some applications, when the core engages, there may be a sharp increase in the slope of the Muscle Engagement Identification Algorithm Input 70. Define inflexionPoint 152*c* as the point before a large increase in the slope of the Muscle Engagement Identification Algorithm Input 70. In an embodiment, if the inflexionPoint 152*c* is less than the engageThreshold and the slope of signal algInput 70 following the inflexion point is high enough to qualify as a Relaxed-to-Engaged 122 trigger as shown in FIG. 15*a*, a Relaxed-to-Engaged 122 may be triggered. If instead the inflexionPoint 152*c* is greater than the engageThreshold as shown in FIG. 15*b*, the Relaxed-to-Engaged 122 trigger may be inhibited.

With reference to FIG. 15*c*, beginning in the Relaxed state 100, calculate the sample-to-sample slope 153*a* of the Muscle Engaged Value 80. When said sample-to-sample slope exceeds a slopeThreshold 153*g* and the inflexion point 152*c* preceding the increase in sample-to-sample slope is less than the engageThreshold 153*d*, Relaxed-to-Engaged 122 may be triggered. If Relaxed-to-Engaged 122 is not triggered, signal algInput 70 may be stored to identify the inflexionPoint 152*c* when a slope increase occurs.

With reference to FIG. 15*d*, an embodiment is described, beginning in the Relaxed state 100. The slope of Muscle Engaged Value is calculated by performing a sample-to-sample difference. In an embodiment, the engageThreshold may be used for the slopeThreshold. Since the slope Δ MEV is the simple difference between the current value of the Muscle Engaged Value[n] and the last value Muscle Engaged Value[n−1], if Δ MEV>engageThreshold 80, the last value Muscle Engaged Value[n−1] may be used as the inflexionPoint 152*c* and also compared with engageThreshold 80 154*b*.

In an embodiment, the location of the inflexion point may not be considered and if the slope of the Muscle Engaged Value equals or exceeds a threshold, Relaxed-to-Engaged 122 may be triggered. And if the slope of the Muscle Engaged Value does not exceed a threshold, Relaxed-to-Engaged 122 may be inhibited.

Other algorithms may be utilized to trigger Relaxed-to-Engaged 122. The different approaches to implementing Relaxed-to-Engaged 122 may be used in isolation or in different combinations. In an embodiment, a technique to implement Relaxed-to-Engaged 122 may be turned on or off by the user 100. In an embodiment, control parameters for techniques to implement Relaxed-to-Engaged 122 may be programmed by the user 100. In embodiment, an approach to implement Relaxed-to-Engaged 122 and the associated control parameters may be programmed by the app for a specific application.

The target muscle may be identified as relaxed and the Algorithm may be in the state Relaxed 1 when the target muscle is engaged. It is also possible that the core may be identified as relaxed and the Algorithm in Relaxed 1 when the user 100 believes their target muscle is engaged. There may be a few responses to remedy these situations which may include the following. First, modifications may be made to the control parameters of the Algorithm. For example, the engageThreshold 88 may be reduced. Second, a different size extender cap 52 may be used. Third, the position of the wearable device 10 may be changed. Fourth, the belt tightness may be modified. Fifth, the user 100 may try using different cues to engage the target muscle. For example if the target muscle is the core, the user 100 may try a cough since coughing may cause the diaphragm to engage to expel air out of the lungs. This may result in other muscles of the core to co-contract, and result in a core engagement. The user 100 may use a cue such as this to establish a connection between their brain and the target muscle. And sixth, the user may work with a trained therapist or trainer to assist with connecting their brain to the target muscle. Once the target muscle begins to contract via effort by the user 100, the feedback provided by the wearable device 10 and app may assist developing the user's ability to engage a target muscle at will.

Engaged-to-Relaxed State Transition 221

When the user's muscle begins to relax, pressure on the Muscle Contraction Sensor may begin to decrease, and the Muscle Engaged Value 80 may being to decrease. In an embodiment, Engaged-to-Relaxed 221 from state Engaged 2 to the state Relaxed 1 may be triggered by one of a multiplicity of events. In an embodiment, Engaged-to-Relaxed 221 may have additional qualifiers to increase confidence that the target muscle has relaxed.

Figures 16A, 16B, 16C:
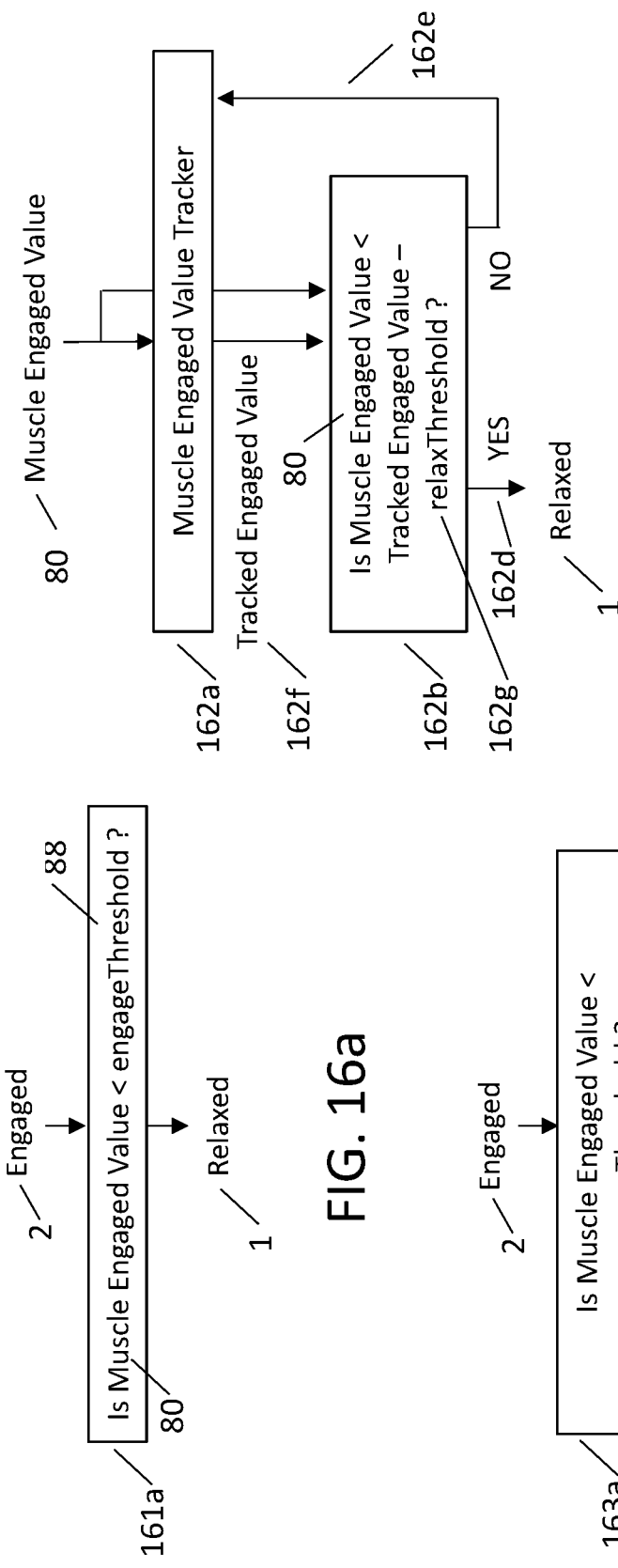
FIG. 16a-FIG. 16c illustrate signal flow diagrams for embodiments for transitioning from the engaged state to the relaxed state.

With reference to FIG. 16*a*, in an embodiment, a trigger for Engaged-to-Relaxed 221 occurs when the Muscle Engaged Value 80 is less than the engageThreshold 88.

In some applications, for example when performing an aerobic exercises, as the body moves in different directions, the wearable device 10 may move away from the body, causing the Muscle Engaged Value 80 to decrease. It is possible that the Muscle Engaged Value 80 may decrease below the engageThreshold 80 even with the core engaged. Depending on how firmly the wearable device 10 is held against the body and where the device is being worn, some movements such as standing up from seated can also result in the Muscle Engaged Value 80 decreasing below the engageThreshold 80. In an embodiment, with reference to FIG. 16*b*, beginning in the Engaged state 200, when the Muscle Engaged Value 80 is less than the engageThreshold 88, the sensor outputs are evaluated for a nominal level of movement. If movement is detected 163*d*, the Engaged-to-Relaxed 221 transition may be inhibited. If movement is not detected 163*c*, then Engaged-to-Relaxed 221 may be triggered.

When the Muscle Engaged Value 80 decreases below the engageThreshold 88, the target muscle may be identified as relaxed. In some applications, when a user 100 relaxes the target muscle from the engaged condition, the pressure may decrease quickly when they first relax and then decrease in the Muscle Engaged Value 80 may slow as the target muscle further relaxes. This slow tail in the return of the Muscle Engaged Value 80 may be referred to as a "slow tail" relax. The slow reduction in the Muscle Engaged Value 80 may in some applications limit the readiness of the system to identify a next movement or target muscle engagement.

With reference to FIG. 16*c*, an embodiment that may reduce the effect of a slow tail relax is shown. Beginning from Engaged 200, the Muscle Engaged Value 80 is input into the Muscle Engaged Value Tracker 162*a* which is a tracking filter which tracks the average value of its input. In an embodiment, the tracking filter may utilize gear shifting. Lowpass filtering the Muscle Engaged Value 80 may reduce noise due to body movements, breathing, and other perturbations. The output of Muscle Engaged Value Tracker 162*a*, the Tracked Engaged Value 162*f*, may be used as reference level. When the Muscle Engaged Value 80 decreases by relaxedThreshold 162*g* below the Tracked Engaged Value 162*f*, a Engaged-to-Relaxed 221 may be triggered. In an embodiment, upon trigger of Engaged-to-Relaxed 221, Muscle Engaged Value 80 may be reset to zero (0); and a Relaxed Minimum Value 124 equal zero (0) may be used. These elements including the flow diagram of FIG. 16*c*, reset of the Muscle Engaged Value 80 to zero (0), and a Relaxed Minimum Value 124 of zero (0) may be used together and may eliminate the slow tail relax. When these elements are used together, upon the Engage-to-Relaxed 221 trigger, the Muscle Engaged Value 80 may crisply transition to zero (0) and remain at zero (0) and the system may be ready for a next engagement of a target muscle.

In an embodiment, the algorithm used to transition from the Engaged state 200 to the Relaxed state 100 may depend on the Engaged Value Tracker 162*f*. If Engaged Value Tracker 162*f* is less than a specific value, for example twice the engageThreshold, the algorithm may identify the transition from Engaged 200 to Relaxed 100 when the Muscle Engaged Value 80 becomes less than the engageThreshold 88. In an embodiment, a relaxThreshold may be used in place of the engageThreshold to identify the transition from Engaged 200 to Relaxed 100 wherein the relaxThreshold is less than the engageThreshold in order to introduce hysteresis. If the Engaged Value Tracker 162*f* output is greater than a value, for example twice the engageThreshold, then an algorithm involving the Engaged Value Tracker 162*f* output may be utilized.

Other algorithms may be utilized to trigger Engaged-to-Relaxed 221. The different approaches to implementing Engaged-to-Relaxed 221 may be used in isolation or in different combinations. In an embodiment, a technique to implement Engaged-to-Relaxed 221 may be turned on or off by the user 100. In an embodiment, control parameters for techniques to implement Engaged-to-Relaxed 221 may be programmed by the user 100. In embodiment, a techniques to implement Engaged-to-Relaxed 221 and control parameters may be programmed by the app for a specific application.

Maximum Voluntary Engagement (MVE)

The well-known parameter Maximum Voluntary Contraction (MVC) may use surface Electromyograph (EMG) to identify the maximum engage intensity of a muscle by measuring the electrical activity in said muscle during a maximum contraction. Maximum Voluntary Engagement (MVE) proposed here, attempts to identify the maximum engage intensity of a muscle by measuring the pressure applied to the Muscle Contraction Sensor 50 during a maximum contraction of a target muscle. In an embodiment, a Maximum Voluntary Engagement or MVE may be identified wherein a user 100 may engage a target muscle to its maximum contraction intensity and the MVE may be provided by the wearable device and app. When the user 100 relaxes the target muscle, 0% MVE may be identified at a Muscle Engaged Value 80 of zero (0). In an embodiment, MVE may be used for different applications. In an embodiment, MVE may be used in an app for multiple reps of an exercise.

Figure 17:
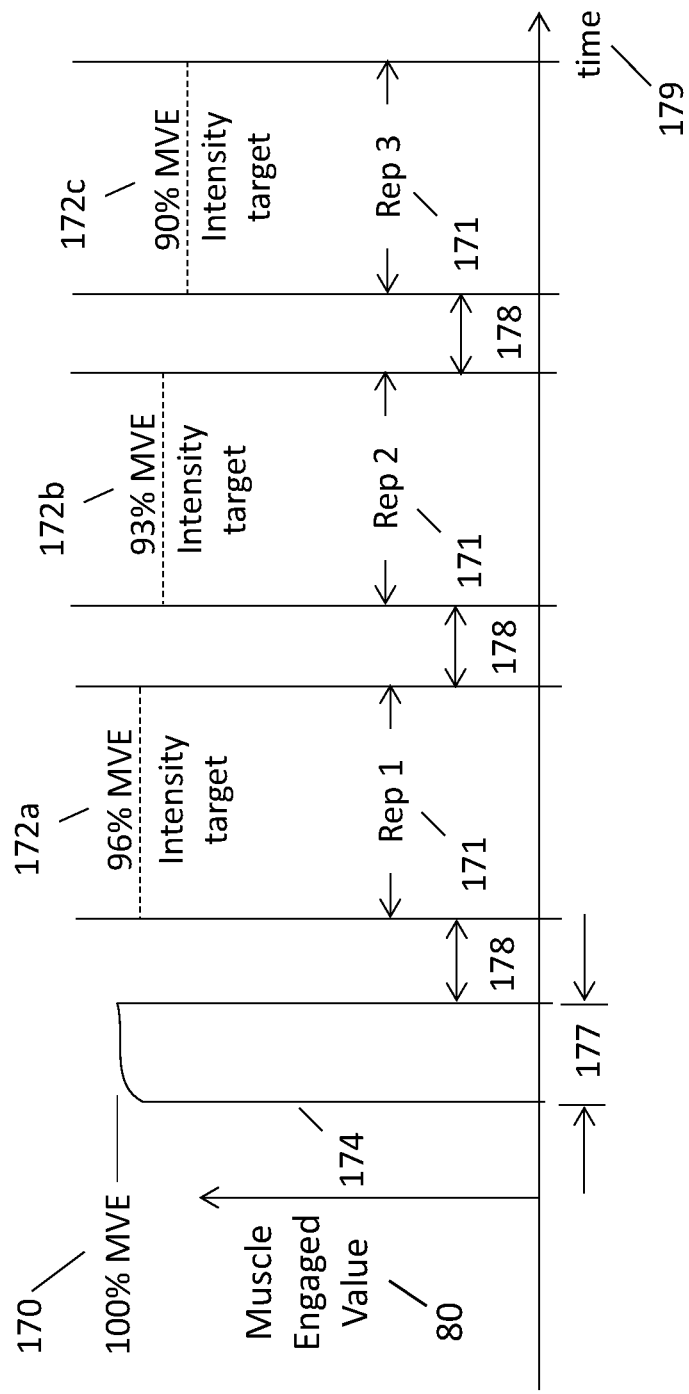
FIG. 17 illustrates an embodiment of a generalized form for performing reps of an isometric exercise with first acquiring an MVE for generating target muscle intensity targets and a score for each rep.

With reference to FIG. 17, the measured Muscle Engaged Value 80 during an example of an exercise with MVE acquisition and MVE use in an exercise target intensity is illustrated. The basic idea is to acquire MVE for a target muscle in a maximum intensity engagement over a short time interval, then use a percentage of the acquired MVE as the engageThreshold for subsequent reps of an exercise. There may be a number of advantages to acquiring an MVE just prior to performing reps of the exercise. The conditions during MVE acquisition and the exercises should be very similar since the MVE is acquired seconds before starting the exercises. The belt tightness and positioning of the wearable device should be very similar for the MVE acquisition and the exercise reps. Since the MVE acquisition happens first, the target muscle should be fresh and this may be a good estimate of the maximum engage intensity. Therefore, a good estimate of the MVE may be acquired with the result that a relevant and objective target intensity for each rep in the exercise is may be available. MVE acquisition and use in exercise targets may be used in a variety of exercises types including isometric and isotonic exercises. To further illustrate the mechanics of MVE acquisition and use in exercise targets, a detailed example of its application to an isometric exercise will be described.

Referring to FIG. 17, the MVE acquisition period and a template for isometric exercise intensity for each rep is shown over time 179. At the beginning of the exercise, the user 100 may begin by placing the body into position and then may be advised to engage the target muscle to its maximum contraction intensity 174 for a short period of time 177. In an embodiment, the short period of time 177 of this MVE acquisition period may be four (4) seconds. A representative sample of the Muscle Engaged Value 80 during this time 177 may be identified as 100% MVE 170 or MVE 170. The MVE 170 may be recorded by the app. Filtering or averaging of the Muscle Engaged Value 80 may be used to generate said representative sample. After a brief rest 178, the user 100 may be advised to return the muscle back into position and perform an isometric hold of the target muscle for the duration of the exercise 171 at an intensity normalized to a percentage of MVE 172*a*-172*c*. In an embodiment, the user 100 may specify the percentage of MVE that will be the target intensity for and throughout each rep 172*a*-172*c*. For example, a user may program three (3) reps of twenty (20) seconds each 171. The user may program 95% MVE for rep 1 172*a*, 90% MVE for rep 2 172*b*, and 85% MVE for reps 3 172*c*. After each rep, the user 100 may have a brief rest, return the muscle back into position, and perform the isometric hold of the target muscle for the duration of the rep until all the reps have been performed. In an embodiment, the percentage of time the user 100 exceeds the target percentage of MVE during a rep may be turned into a score for that rep. In an embodiment, all data, targets, and outcomes may be recorded by the app.

Figure 18:
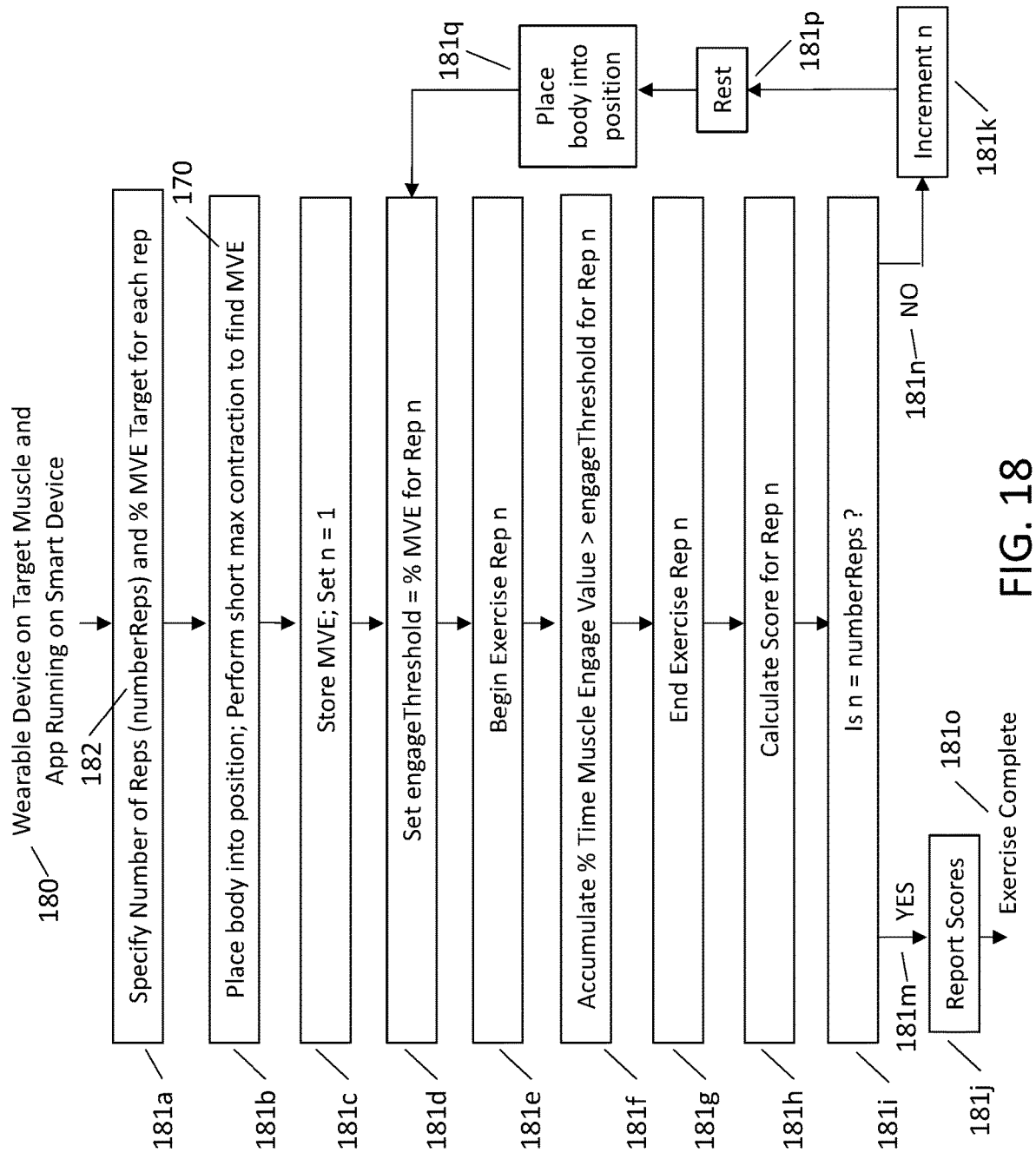
FIG. 18 illustrates a signal flow diagram for an embodiment of multiple reps of an isometric exercise with first acquiring an MVE and using the MVE for generating target muscle intensity and a score for each rep.

With reference to FIG. 18, a flow diagram for an embodiment performing an isometric exercise with the wearable device 10 and app with MVE acquisition and MVE use in an exercise target is presented. Begin by placing the wearable device on the target muscle and starting the app 180. Next, specify the number of reps (numberReps) 182 and the % MVE target for each rep 181*a*. Next, place the body into position and perform a short contraction at maximum intensity to determine MVE 170. Store MVE and setup first rep 181*c*. Set 172 engageThreshold 88 for rep n as a percentage of MVE 181*d*. Begin exercise rep n 181*e*. Accumulate the percentage of time the Muscle Engaged Value 80 exceeds the engageThreshold 172 181*f*. End the exercise rep 181*g* and calculate a score for the rep 181*h*. If the number of reps completed is less than numberReps 182, then increment n 181, rest 181p, return the body into position 181q, set 172 engageThreshold 88 for the next rep and begin the next rep 181e. When the number of reps completed equals numberReps 182, report scores to the user 181j and end the exercise 181o.

In an embodiment, the order of placing the body into position and then engaging the target muscle may be switched. It may instead be beneficial to engage the target muscle and then place the body into position.

Performing an exercise using the wearable device 10 and app following this procedure may increase the quality and consistency of the exercise via the objective targets and performance measures. By maintaining records for an exercise that may include the selection of the number of reps, duration of reps, measurement of belt tightness when the target muscle is relaxed (measured using the raw Muscle Contraction Sensor data), measurement of the MVE, % MVE achieved for each rep, scores for each rep, and date and time the exercise is performed, exercise progress may be effectively tracked. With the new elements made available by the wearable device 10 and app for exercise regimens such as increased accountability from progress tracking, quantitative exercise targets, and objective feedback, exercise effectiveness and exercise experience may be improved for the user 100. In an embodiment, records for an exercise may be stored and reported to the user 100 and others such as a therapist, trainer, coach, or doctor.

Figure 19:
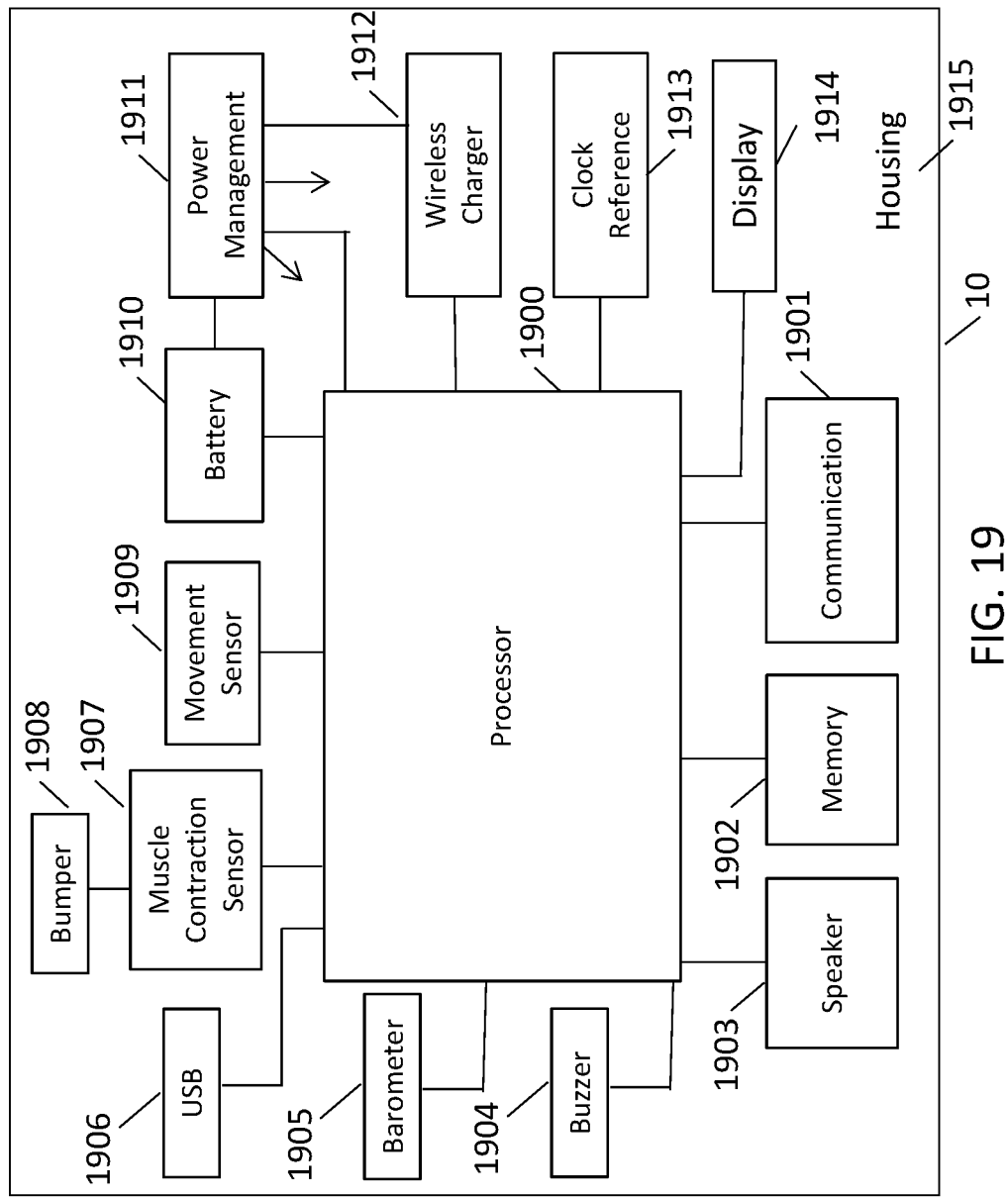
FIG. 19 illustrates a block diagram of the electronics related functional blocks inside the wearable device.

With reference to FIG. 19, a block diagram of an embodiment of the wearable device 10 is illustrated. All elements and components may reside in housing 1915. A processor 1900 may run program code, communication protocols, and control the overall system. The processor 1900 may be coupled to a communication device 1901 that may transmit information and data to other devices through a wired or wireless communications connection, for example the communications device 1901 may utilize Bluetooth technology or WiFi technology that may provide wireless communication with other devices and enable firmware updates. A battery 1910 may be coupled to a power management module 1911 which may control the distribution of electrical power to the system components. The battery 1910 may be rechargeable and capable of being charged with a charger. USB module 1906 may be used for battery charging, loading program code, and firmware updates. A wireless charger 1912 may be used for battery charging. The processor 1900 may also be coupled to memory 1902 which may store program code and sensor, time-stamp, and other data. The memory 1902 may store or record raw data, partial results, or complete results from the processor 1900 utilizing digital signal processing. A clock or timing reference 1913 may provide a system reference clock to the processor 1900 which may also be used to derive sampling clocks for the sensors. If the system has a minimum of intermittent access to date and time information, for example through a cellular system or smart device, the clock reference 1913 may be utilized in an algorithm using said date and time information to enable recorded data and any other results to be stored with time stamps. Muscle contraction sensor 1907 may acquire muscle contraction data. Bumper 1908 may couple to muscle contraction sensor 1907 and extrude from the housing 1915 to couple to a target muscle. Movement sensor 1909 may acquire movement data and may include a gyro and an accelerometer for measuring rotation, acceleration, and orientation. Barometer 1905 may acquire data from movements involving changes in elevation. Movement sensor 1909 may include other sensor types for acquiring other movement data. Buzzer 1904 may provide feedback to the user 100. Speaker 1903 may provide instruction and audio feedback to the user 100. Speaker 1903 may function as a microphone, enabling the user 100 to change modes and control parameters via voice control. A display 1914 may enable system control, instruction, status and Algorithm data, and other data to be input to the system and output from the system. Display 1914 may include a touch screen. Housing 1915 may include an element to secure the bumper 1908. In some embodiments, some of the elements and components shown in FIG. 19 may not be included. In some embodiments, elements and components not shown in FIG. 19 may be included.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Some embodiments of the invention are implemented as a program product for use with an embedded processor. The program(s) of the program product defines functions of the embodiments (including the methods described herein) and can be contained on a variety of signal-bearing media. Illustrative signal-bearing media include, but are not limited to: (i) information permanently stored on non-writable storage media; (ii) alterable information stored on writable storage media; and (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the process is described with reference to a device, system, and method for developing rhythmic breathing, the process may be used in other contexts as well. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

What is claimed is:

1. A system for development of muscles, comprising:
a contraction sensor for detecting a muscle contraction;
an elastic bumper coupled to the contraction sensor wherein the elastic bumper is placed against the muscles;
a belt holding the contraction sensor and the elastic bumper over the muscle;
a movement sensor for detecting body movements;
a processor coupled to the contraction sensor for receiving muscle contraction signals from the contraction sensor and body movement signals from the movement sensor wherein the processor determines a muscle engagement value from the muscle contraction signals that are between zero and a 100% maximum engagement value based upon the muscle contraction signals; and
a display coupled to the processor wherein the display displays the muscle engagement value and body movement data simultaneously.

2. The system of claim 1 further comprising:
a sensor housing coupled to the belt, the sensor housing containing the contraction sensor wherein the elastic bumper extends outward from a surface of the housing.

3. The system of claim 1 further comprising:
an extender cap that includes a recessed interface surface that is placed over a portion of the elastic bumper, the extender cap having a height, a girth, and an exposed convex surface that is placed against the muscle.

4. The system of claim 3 further comprising:
a second extender cap with a second height and a second girth wherein the second height is different than the height of the extender cap and the second extender cap replaces the extender cap on the elastic bumper.

5. The system of claim 1 further comprising:
an annular extender placed around a portion of the elastic bumper.

6. The system of claim 1 wherein the elastic bumper is an annular structure.

7. The system of claim 1 further comprising:
a non-linearity compensation program running on the processor for correcting the muscle contraction signals from the sensor wherein the non-linearity compensation program creates a linear correction of the muscle contraction signals from the contraction sensor.

8. The system of claim 6 further comprising:
a programmable gain for amplifying the muscle contraction signals after the linear correction.

9. A system for development of a limb muscle, comprising:
a contraction sensor for detecting a limb muscle contraction;
an elastic bumper to couple the contraction sensor wherein the elastic bumper is placed against the limb muscle;
a belt holding the contraction sensor and the elastic bumper over the limb muscle;
a movement sensor for detecting body movements;
a processor coupled to the contraction sensor for receiving limb muscle contraction signals from the sensor and body movement signals from the movement sensor wherein the processor determines limb muscle engagement values that are between zero and a 100% maximum engagement value from the muscle contraction signals based upon the limb muscle contraction signal; and
a display coupled to the processor wherein the display displays limb muscle engagement value and body movement data simultaneously.

10. The system of claim 9 further comprising:
a sensor housing coupled to the belt, the sensor housing containing the contraction sensor wherein the elastic bumper extends from a surface of the housing.

11. The system of claim 9 further comprising:
an extender cap placed over a portion of the elastic bumper wherein the extender cap includes a recessed interface surface that is placed over a portion of the elastic bumper, the extender cap having an exposed convex surface that is placed against the limb muscle.

12. The system of claim 9 further comprising:
an annular extender cap placed around a portion of the elastic bumper.

13. The system of claim 9 wherein the elastic bumper is an annular structure.

14. The system of claim 9 further comprising:
a non-linearity compensation program running on the processor for correcting the core limb muscle contraction signals from the sensor wherein the non-linearity compensation program creates a linear correction of the limb muscle contraction signals from the contraction sensor.

15. The system of claim 14 further comprising:
a programmable gain for amplifying the limb muscle contraction signals after the linear correction.

* * * * *